(12) United States Patent
Fujii et al.

(10) Patent No.: US 7,643,143 B2
(45) Date of Patent: Jan. 5, 2010

(54) PARTICLE IMAGE ANALYZING APPARATUS

(75) Inventors: Kozo Fujii, Akashi (JP); Katsuaki Yamaguchi, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 352 days.

(21) Appl. No.: 11/803,604

(22) Filed: May 15, 2007

(65) Prior Publication Data

US 2007/0273878 A1 Nov. 29, 2007

(30) Foreign Application Priority Data

May 15, 2006 (JP) .............................. 2006-135033

(51) Int. Cl.
*G01N 15/02* (2006.01)
*G06K 9/56* (2006.01)

(52) U.S. Cl. ........................ 356/336; 356/338; 382/129; 382/279

(58) Field of Classification Search ......... 356/335–343; 382/100, 205, 129, 279, 321
See application file for complete search history.

(56) References Cited

U.S. PATENT DOCUMENTS 5,471,298 A * 11/1995 Moriya ....................... 356/336
5,721,433 A * 2/1998 Kosaka ....................... 250/573
6,289,126 B1 * 9/2001 Ishisaka ...................... 382/205
7,349,084 B2 * 3/2008 Kusuzawa ................... 356/335
2009/0226031 A1 * 9/2009 Izuka .......................... 382/100

FOREIGN PATENT DOCUMENTS

| EP | 1 245 945 A2 | 10/2002 |
| JP | 2000-131616 | 5/2000 |

* cited by examiner

*Primary Examiner*—Hoa Q Pham
(74) *Attorney, Agent, or Firm*—Brinks Hofer Gilson & Lione

(57) ABSTRACT

A particle image analyzing apparatus for analyzing an image of an imaged particle, the particle image analyzing apparatus comprising: an illuminating unit for providing dark field illumination the a particle; an imaging unit for acquiring capturing an imaged image by imaging the dark field illuminated particle; and an image processing unit for extracting a particle image from the imaged image captured by the imaging unit, based on a threshold value larger than a luminance value substantially corresponding to the background of the particle image, and analyzing the extracted particle image to obtain morphological feature information indicating the morphological feature of the particle; wherein the image processing unit extracts the particle image from the imaged image based on a threshold value larger than a luminance value substantially corresponding to the background of the particle image.

15 Claims, 25 Drawing Sheets

[Fig. 1]
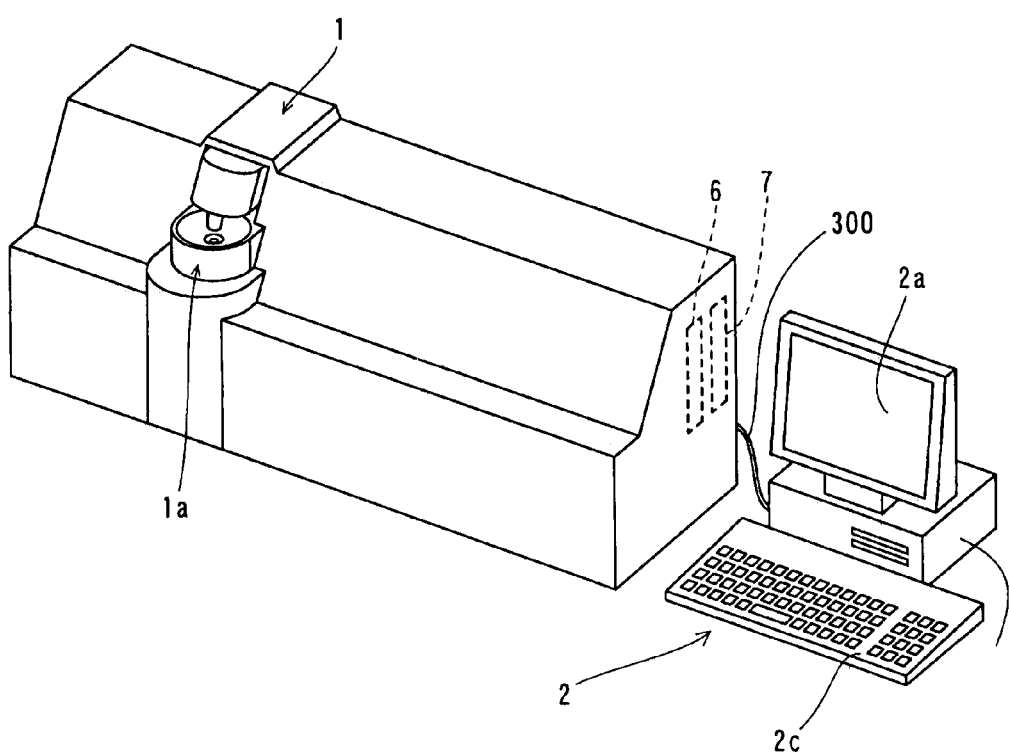

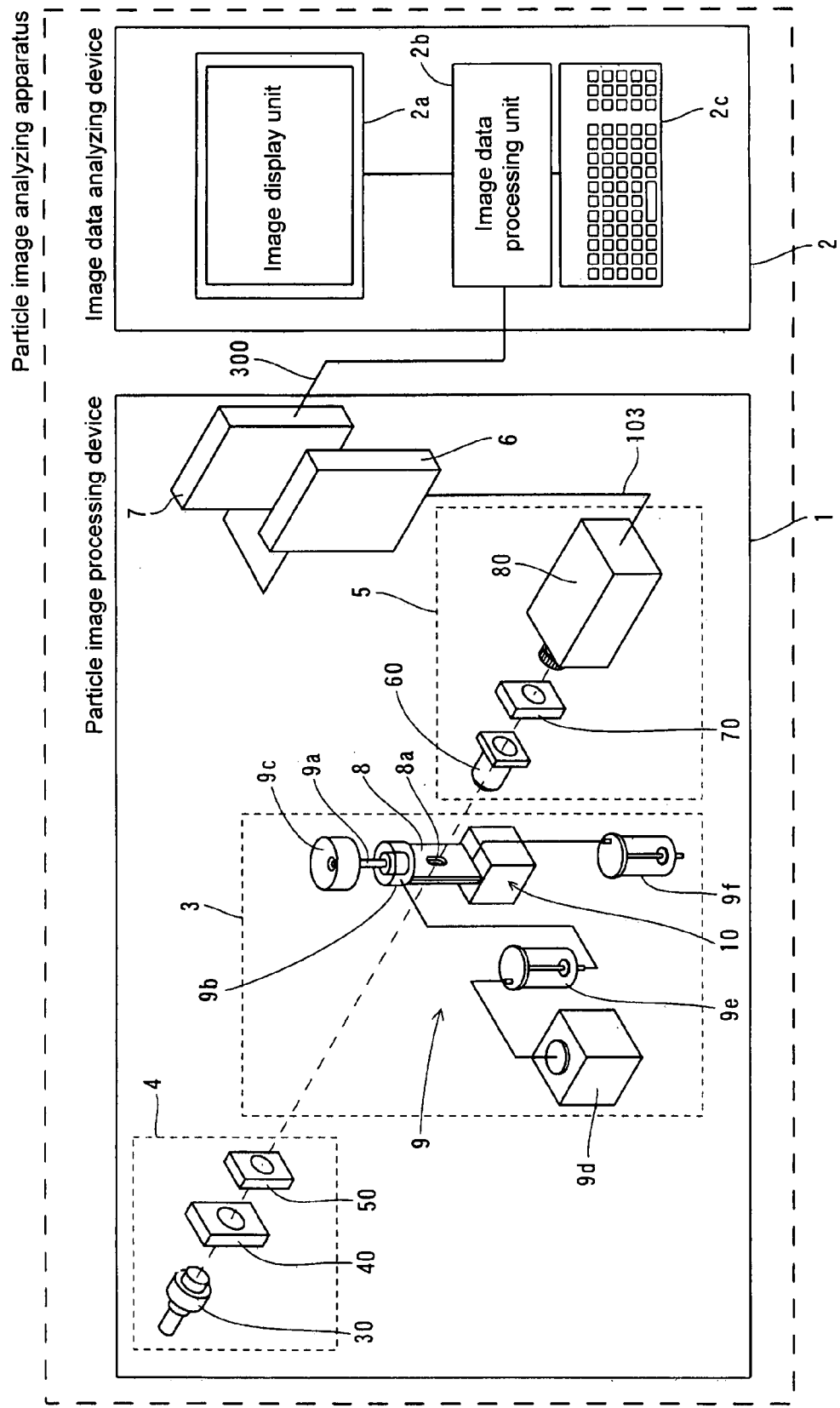
[Fig. 2]

[Fig. 3]
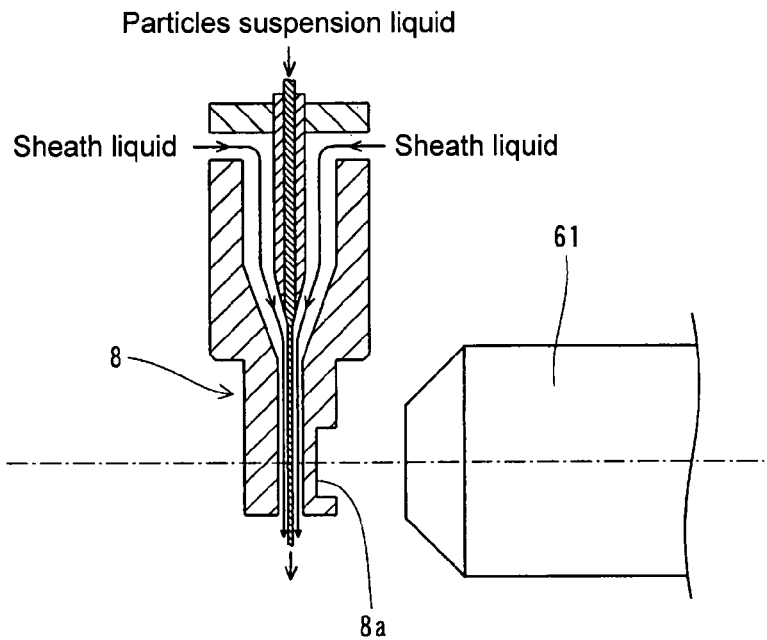
[Fig. 4]
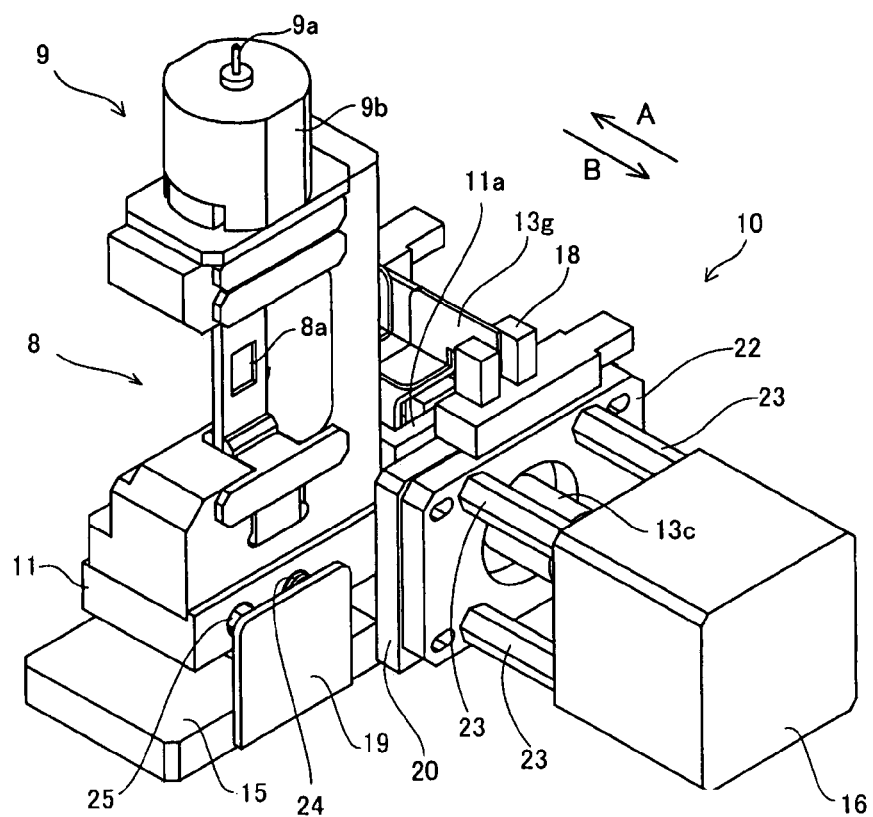

[Fig. 5]
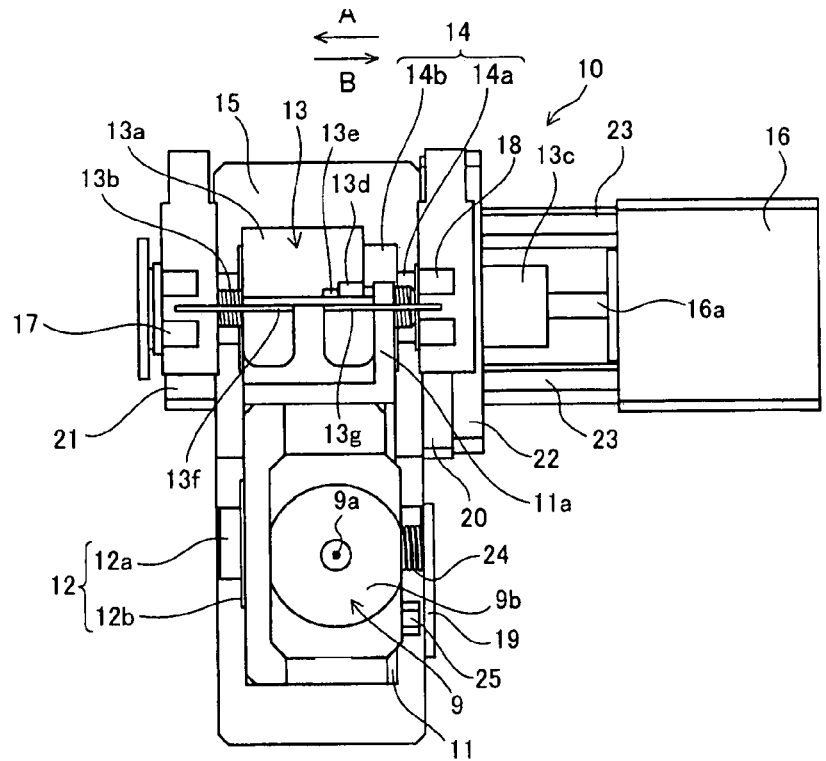
[Fig. 6]
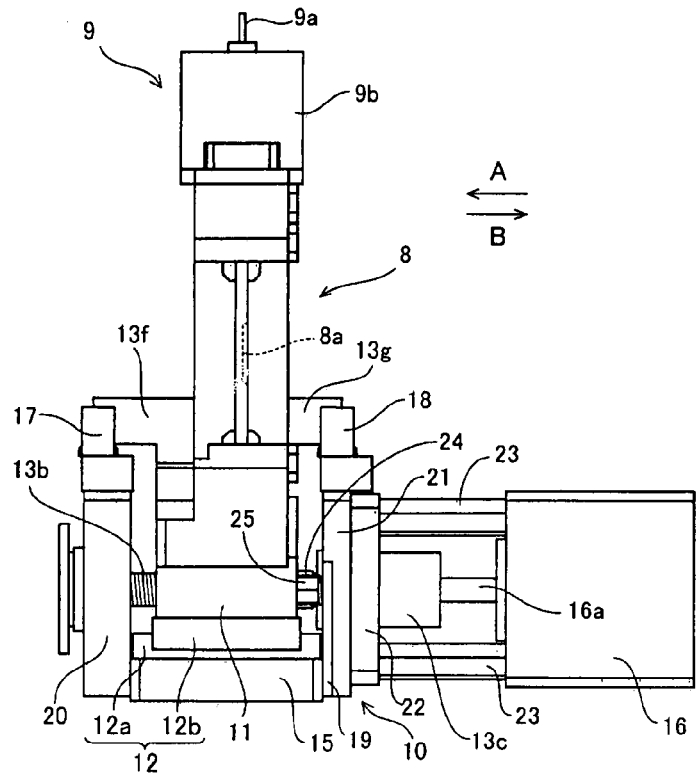

[Fig. 7]
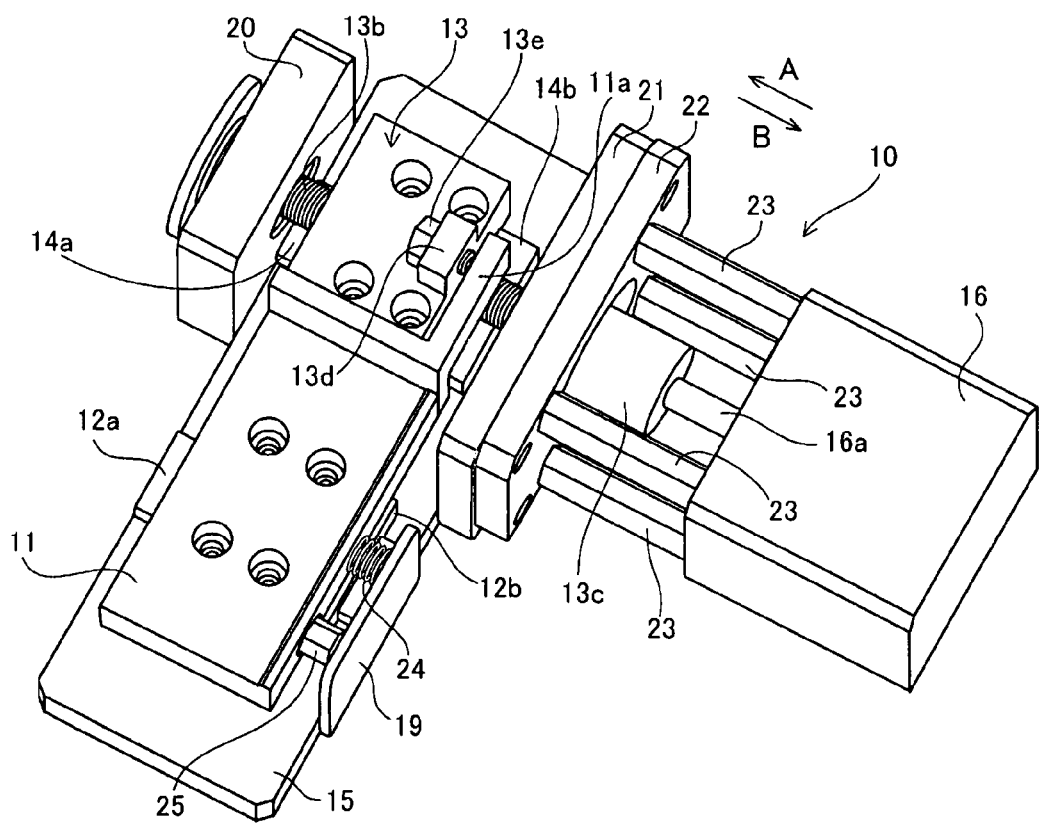

[Fig. 8]
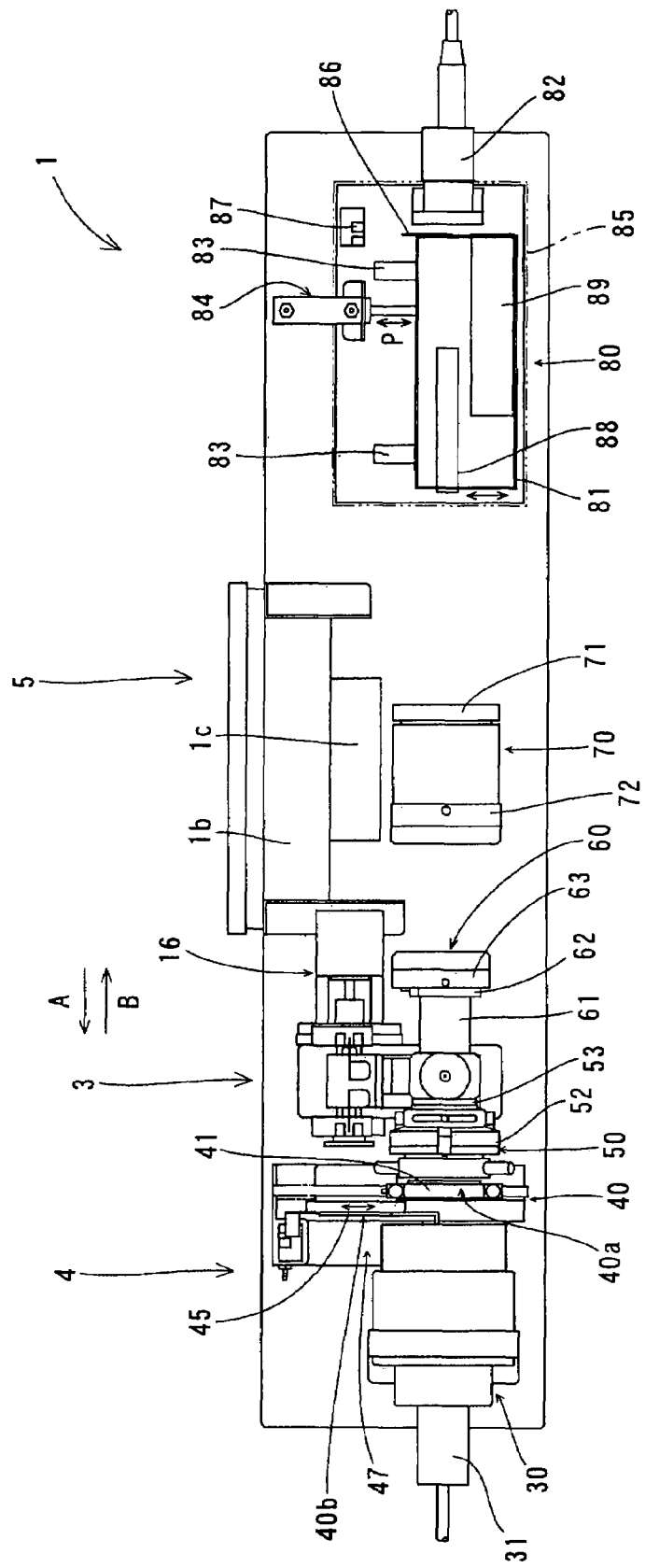

[Fig. 9]
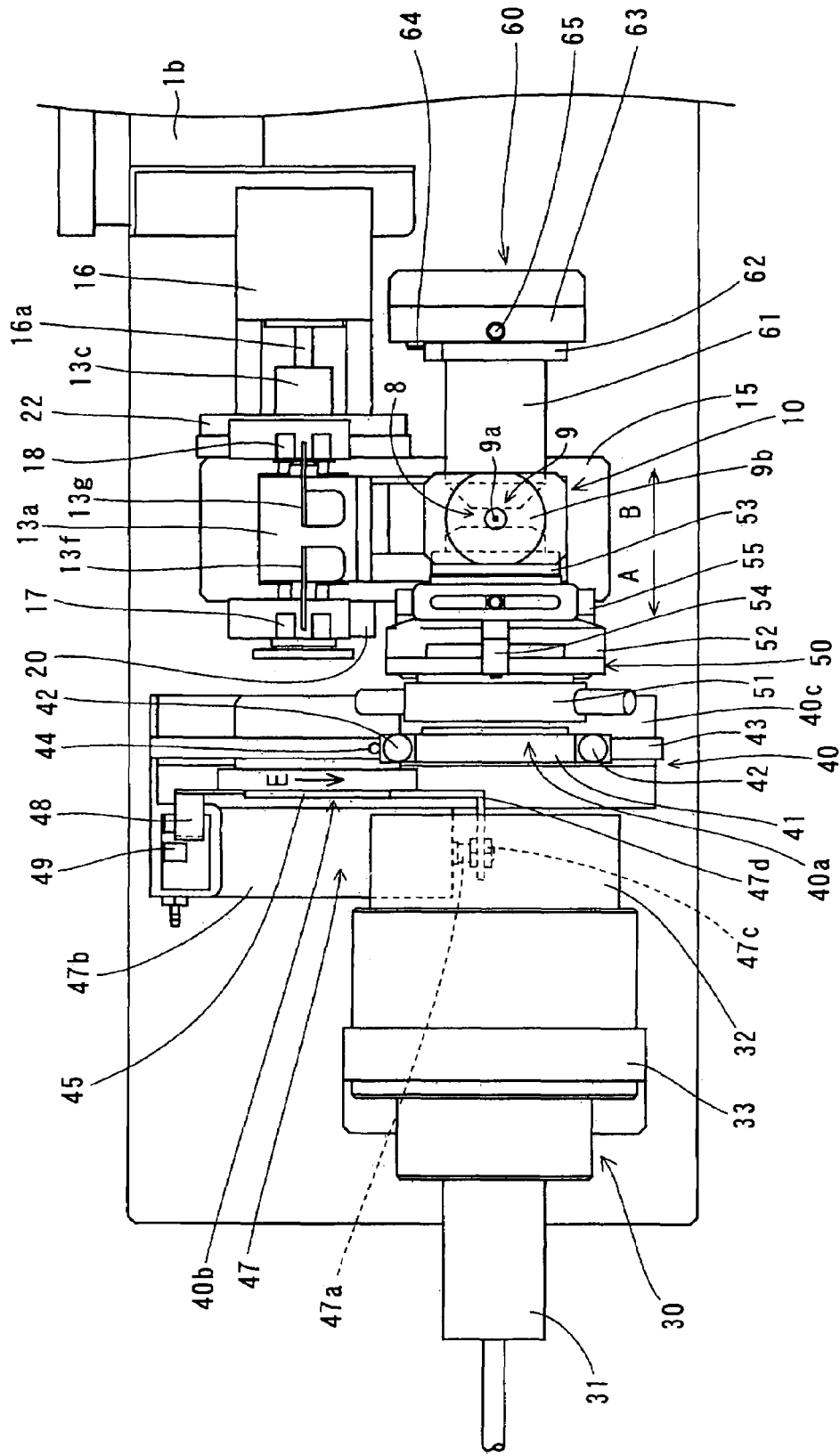

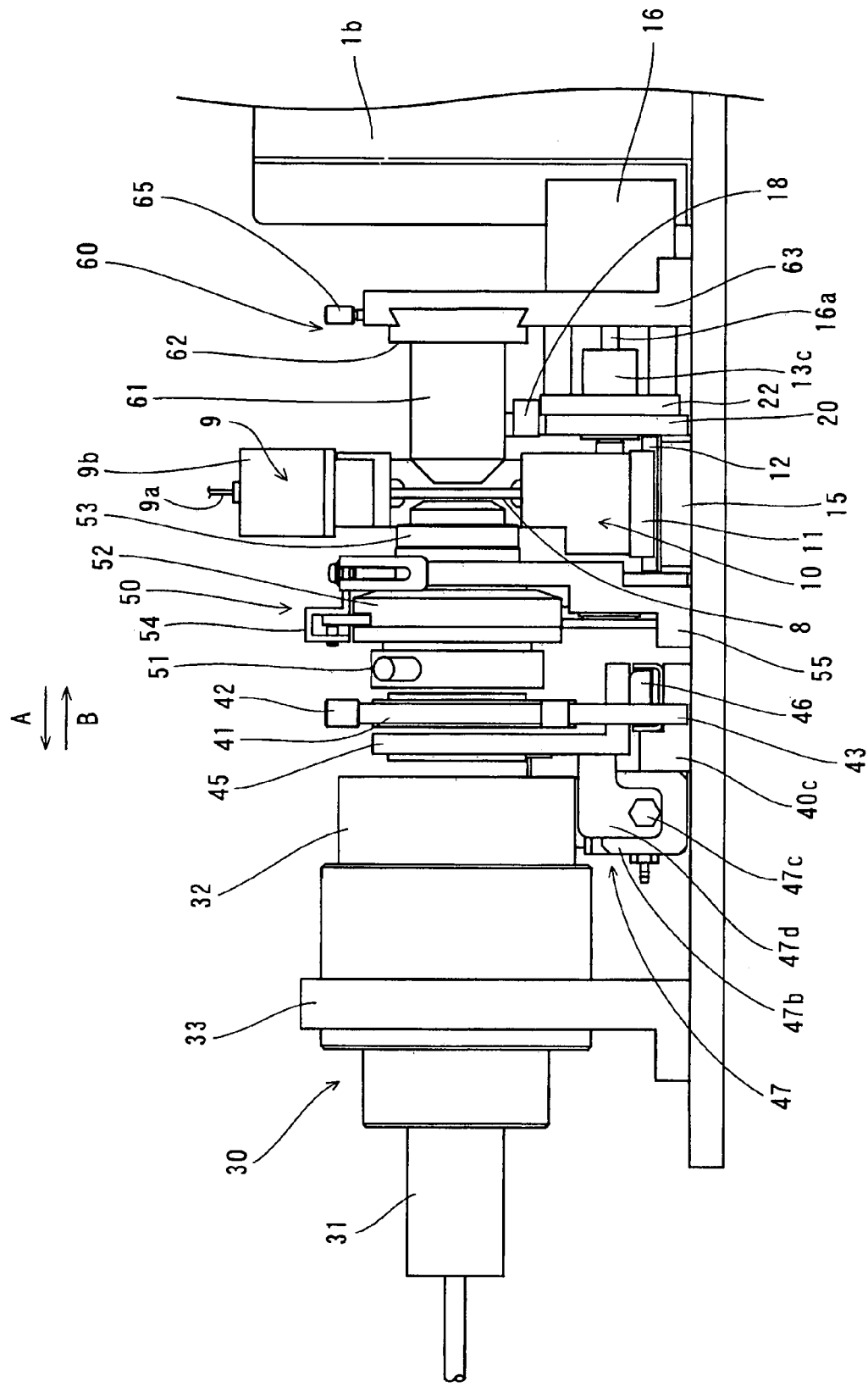
[Fig. 10]

[Fig. 11]
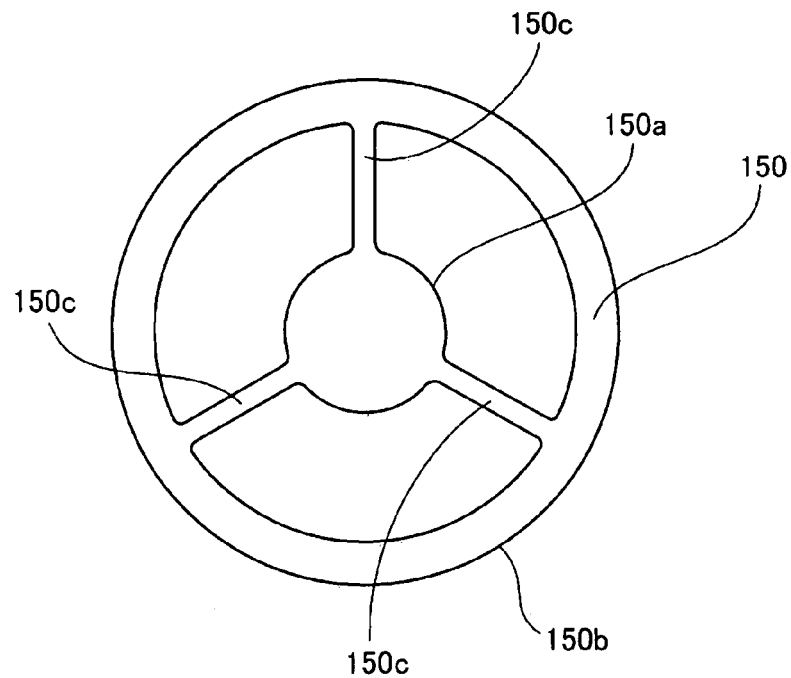
[Fig. 12]
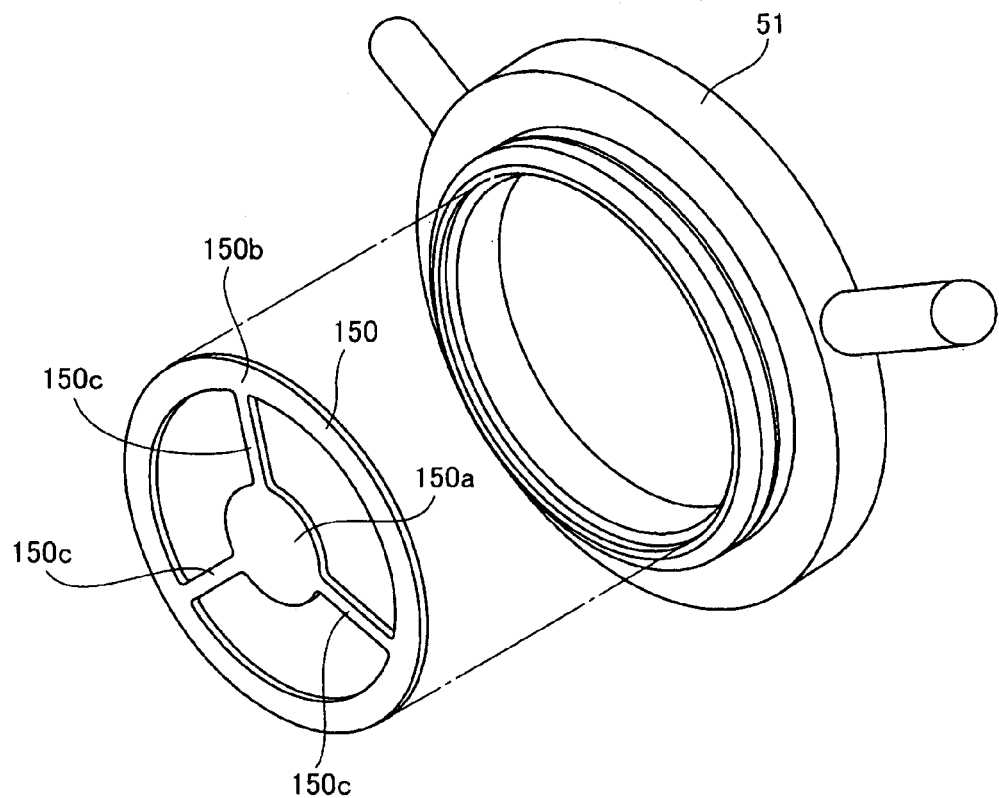

[Fig. 13]
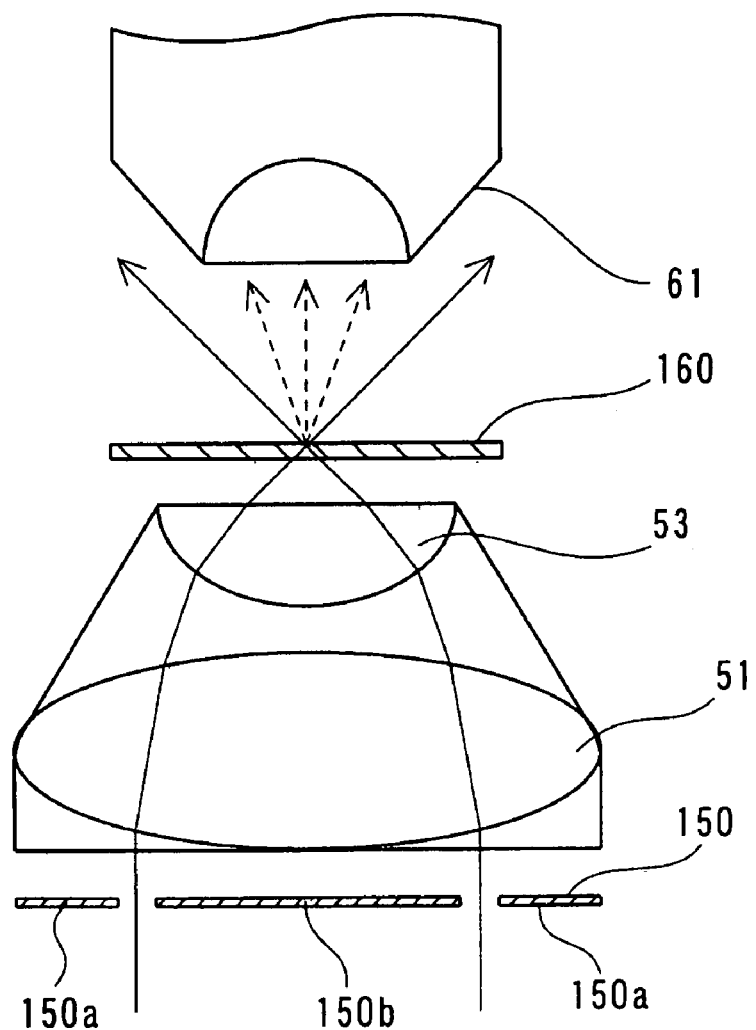

[Fig. 14]
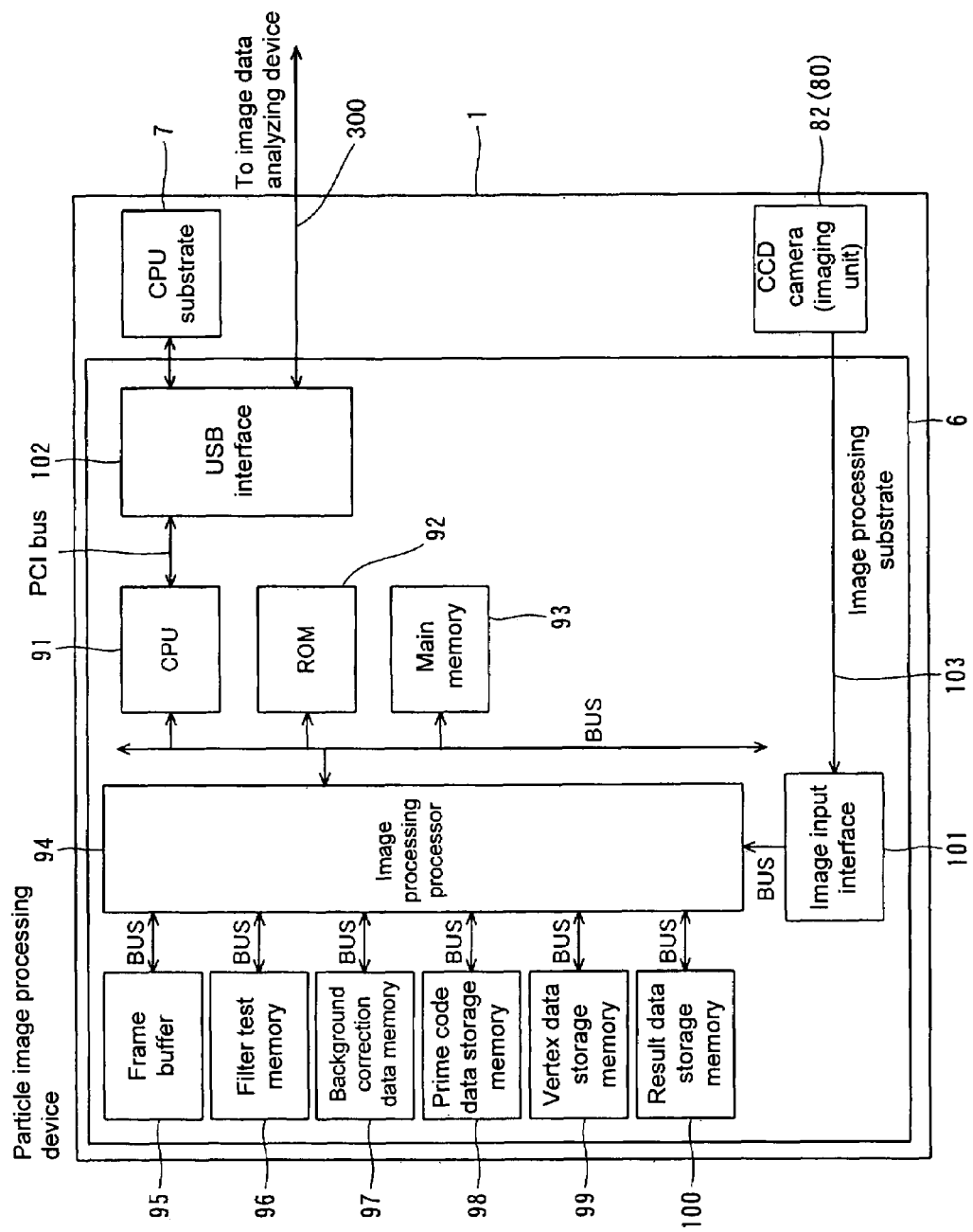

[Fig. 15]
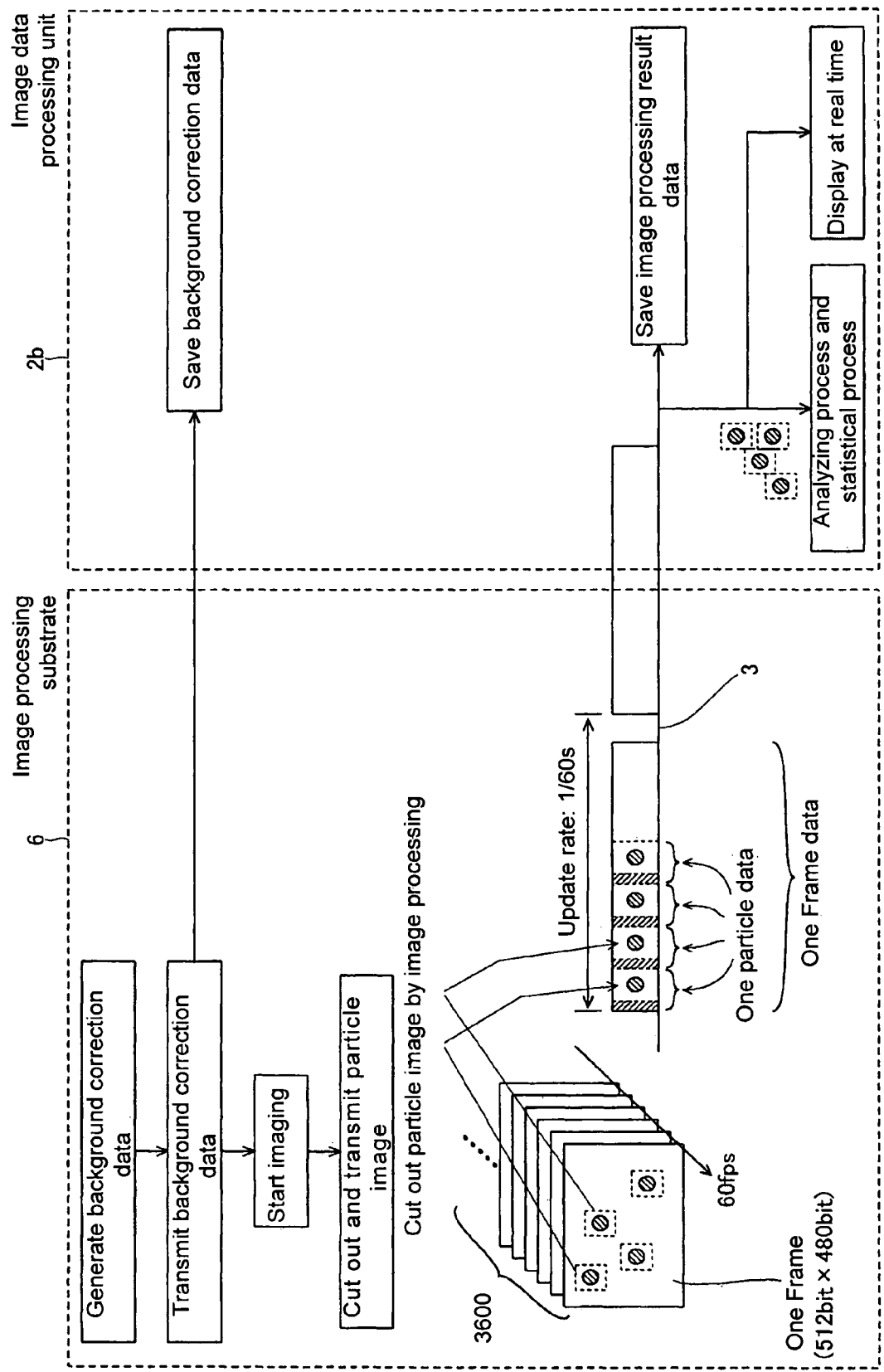

[Fig. 16]
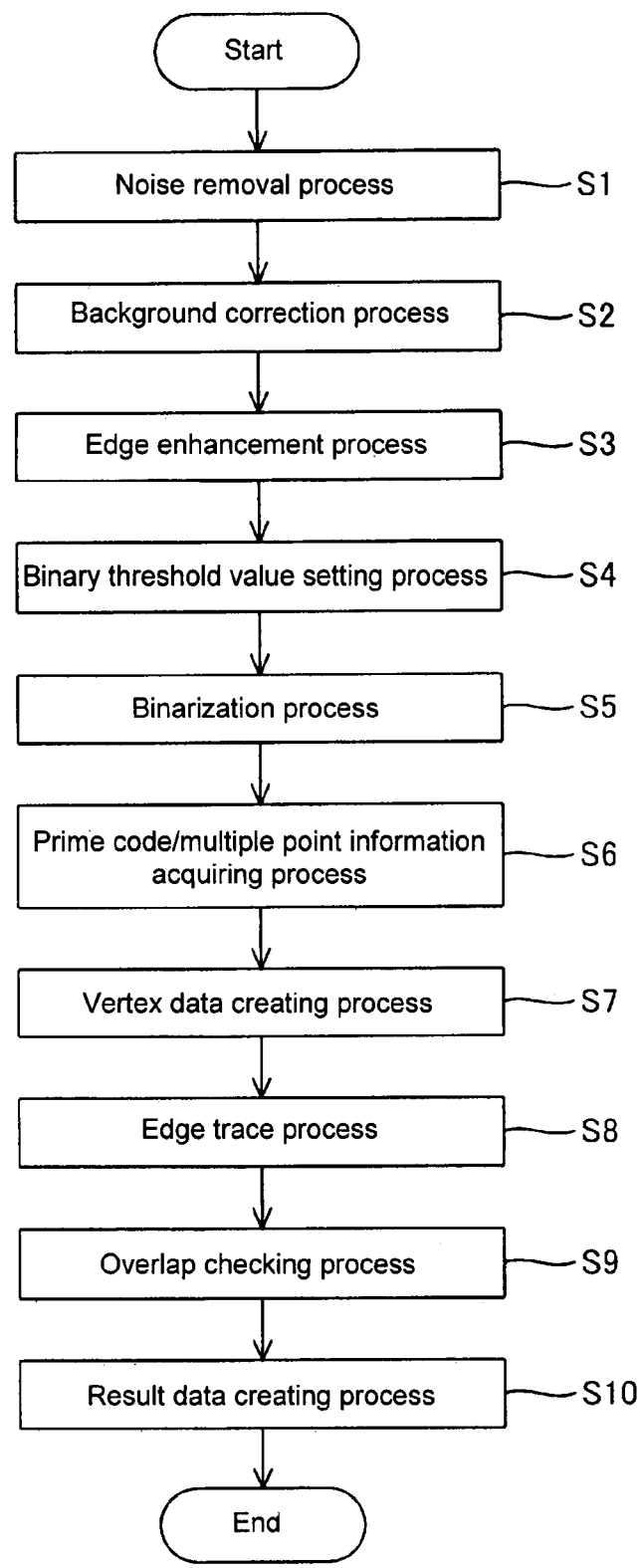

[Fig. 17]
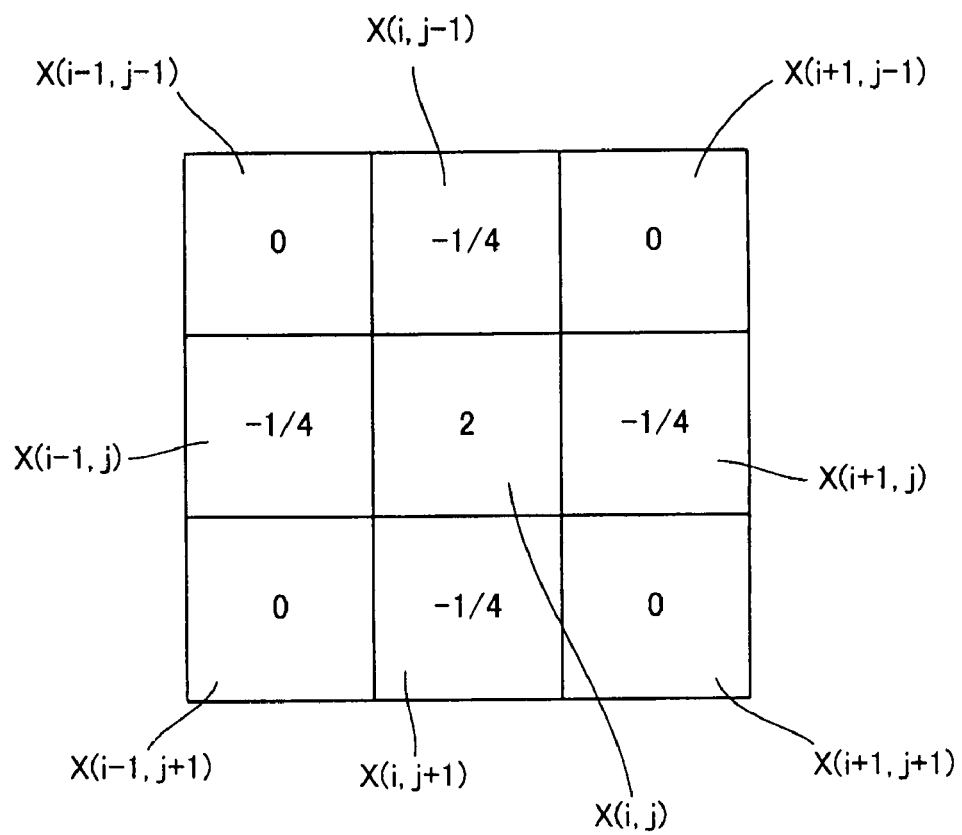

[Fig. 18]
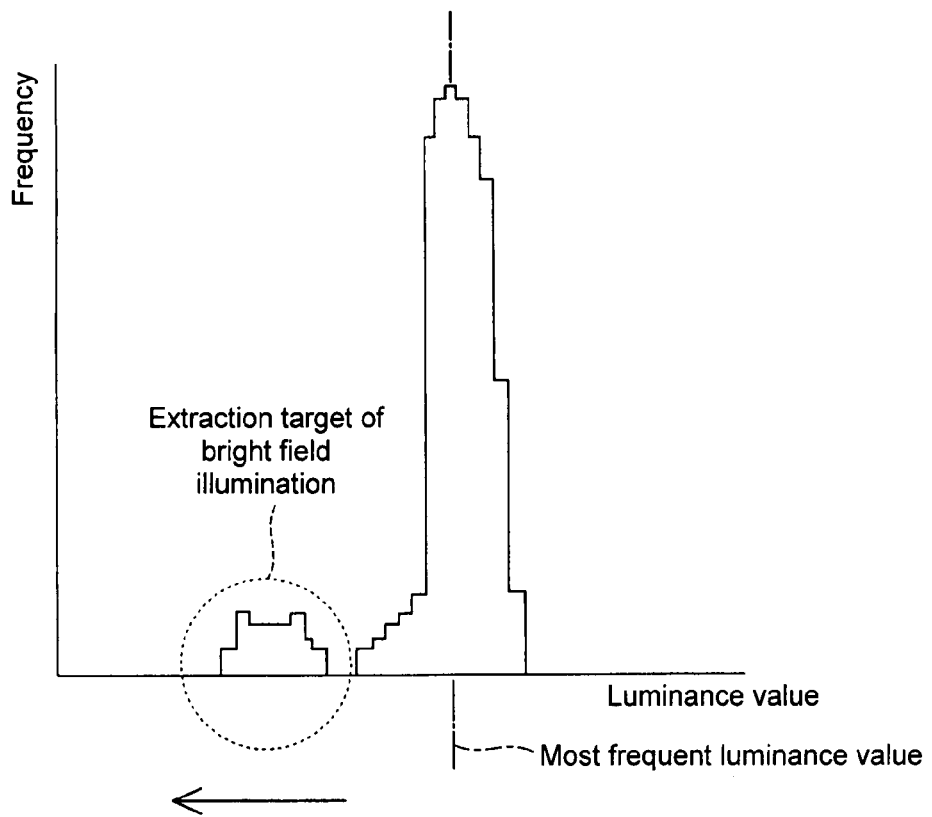

[Fig. 19]
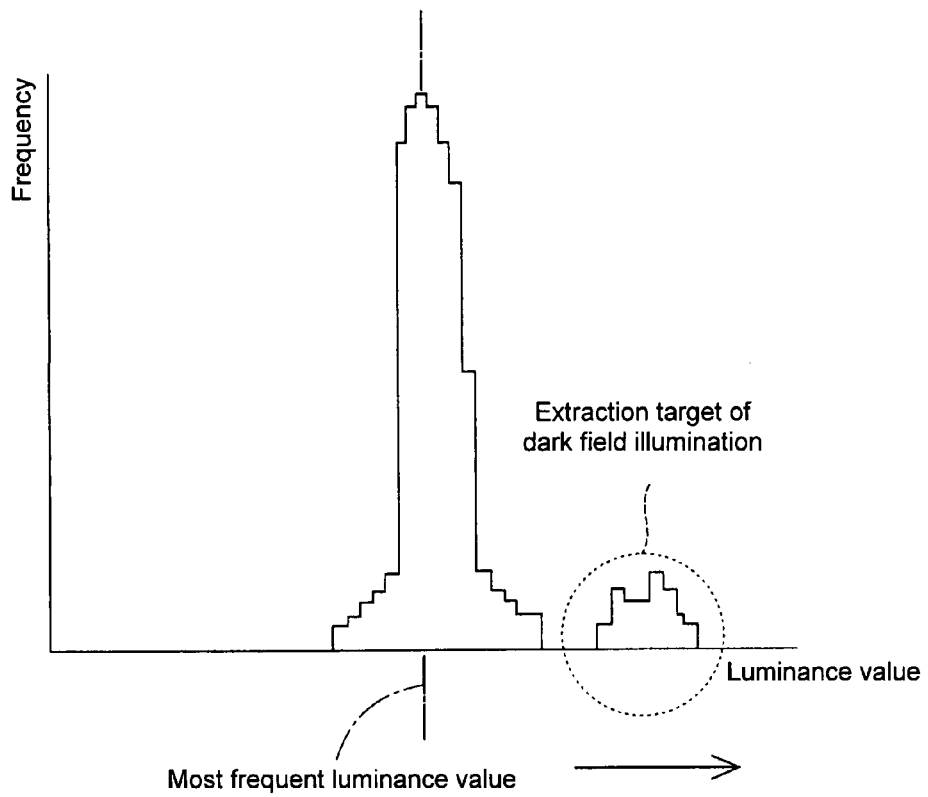
[Fig. 20]
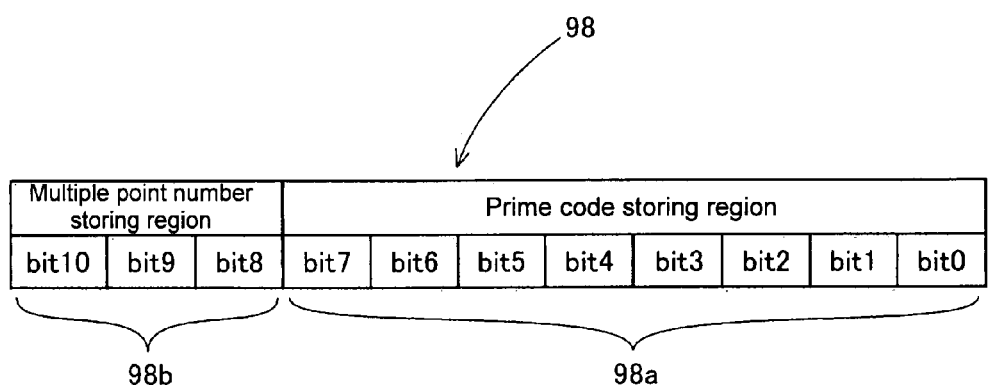

[Fig. 21]
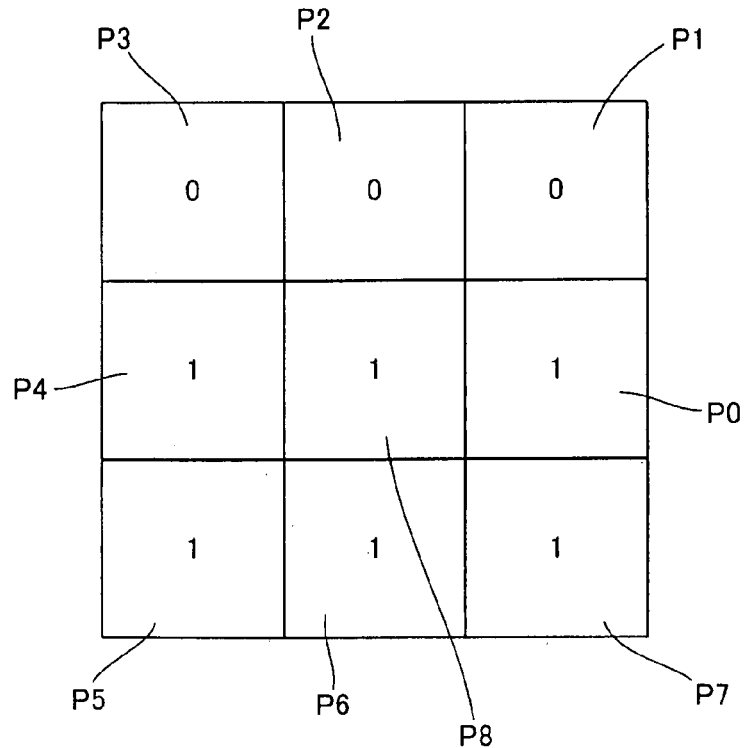
[Fig. 22]
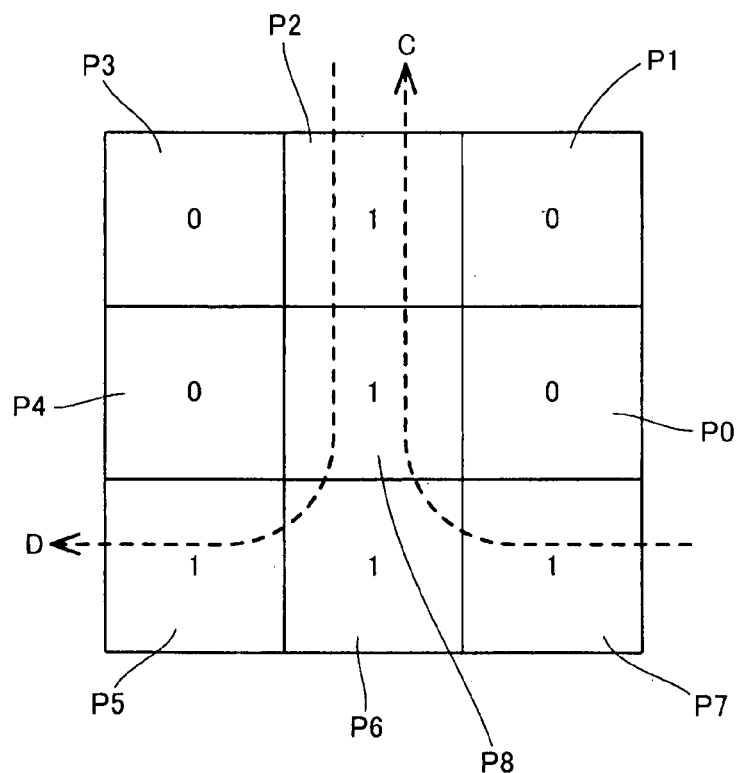

[Fig. 23]
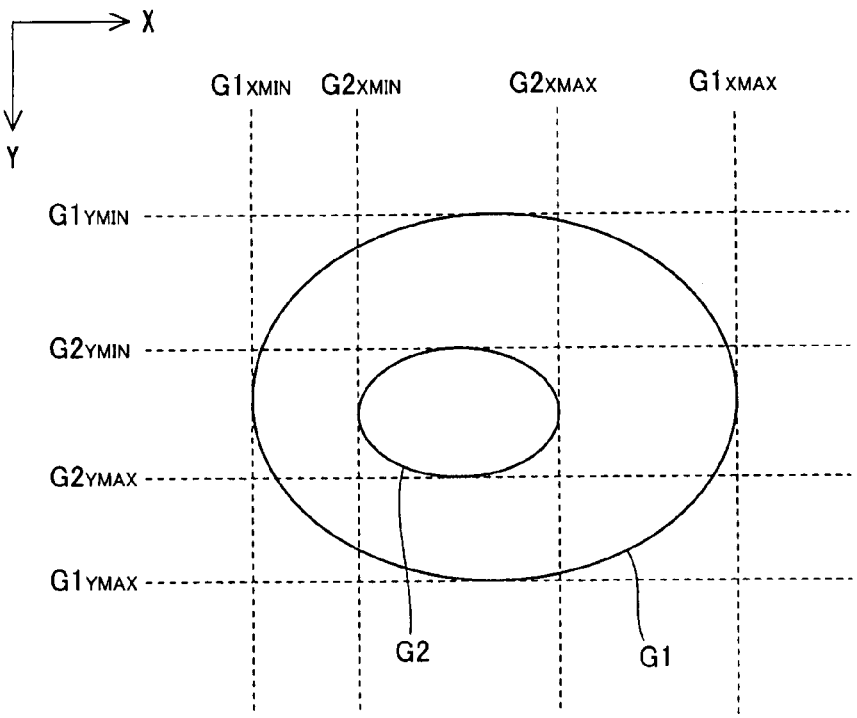
[Fig. 24]
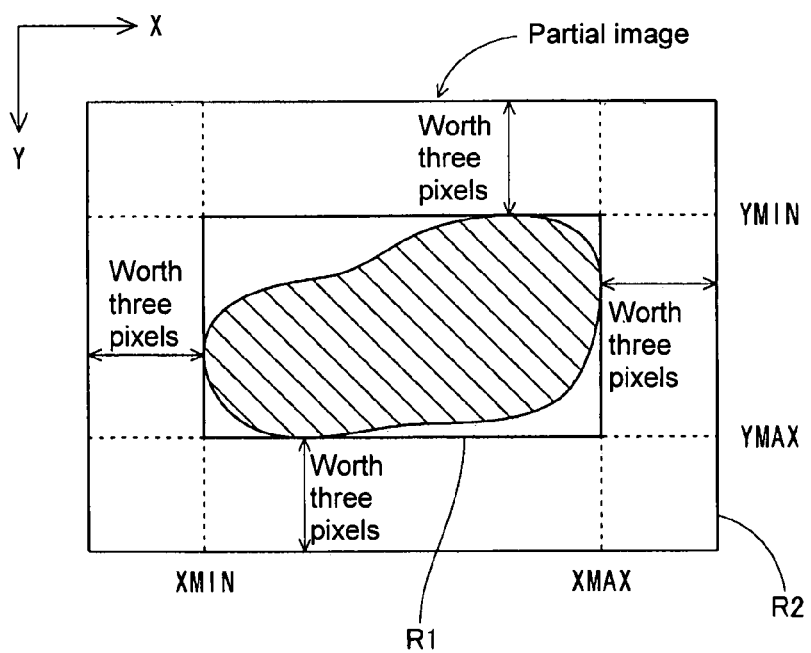

[Fig. 25]
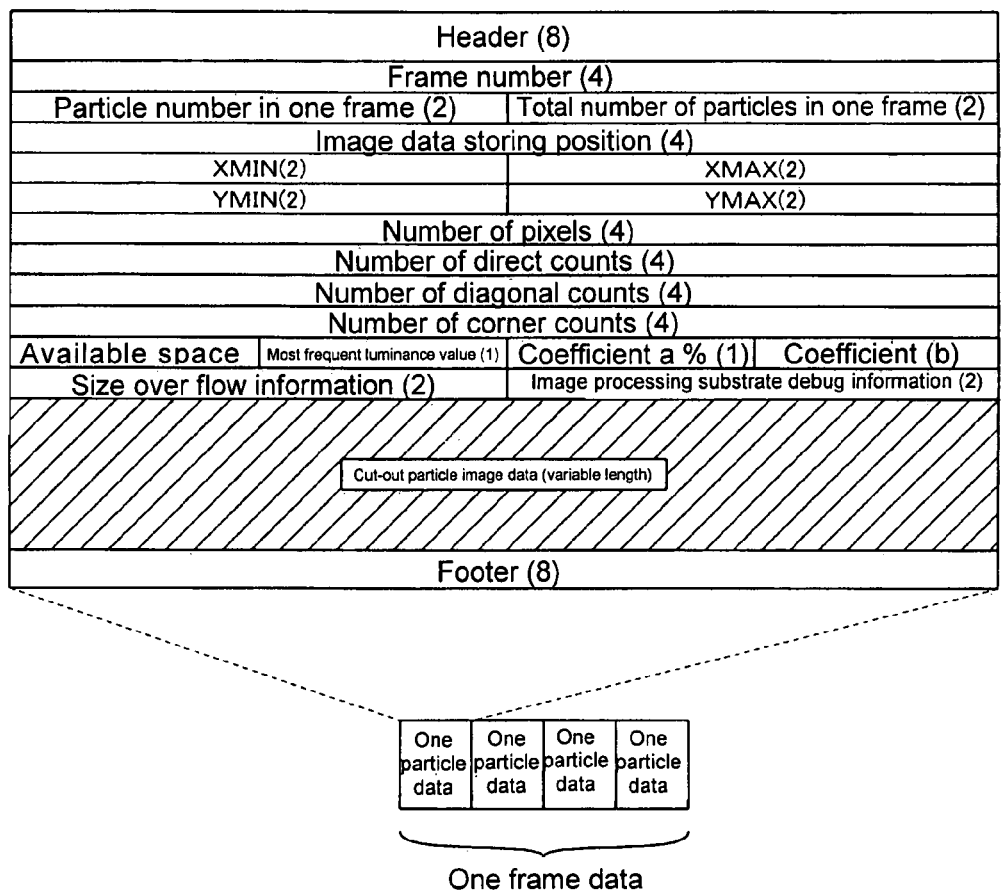

[Fig. 26]
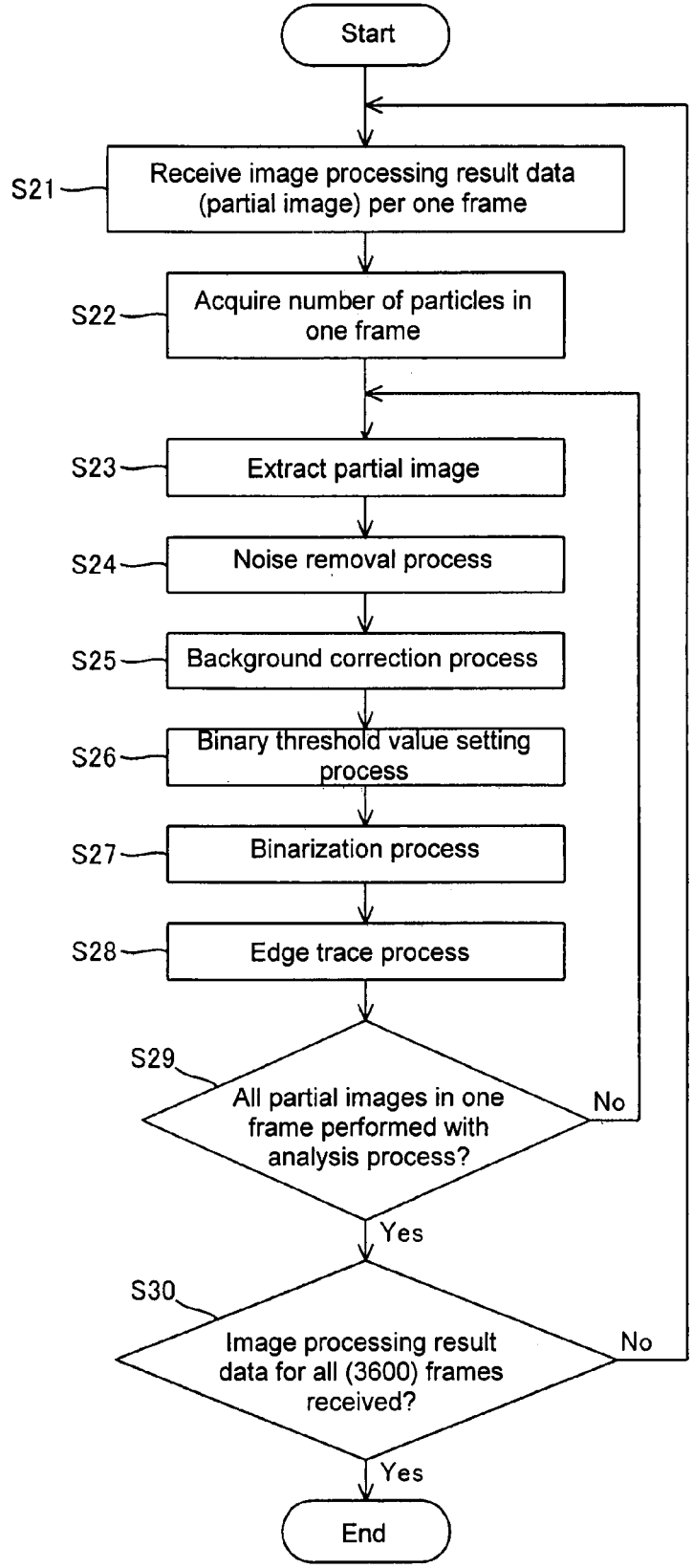

[Fig. 27]
Operation flow of automatic focusing adjustment
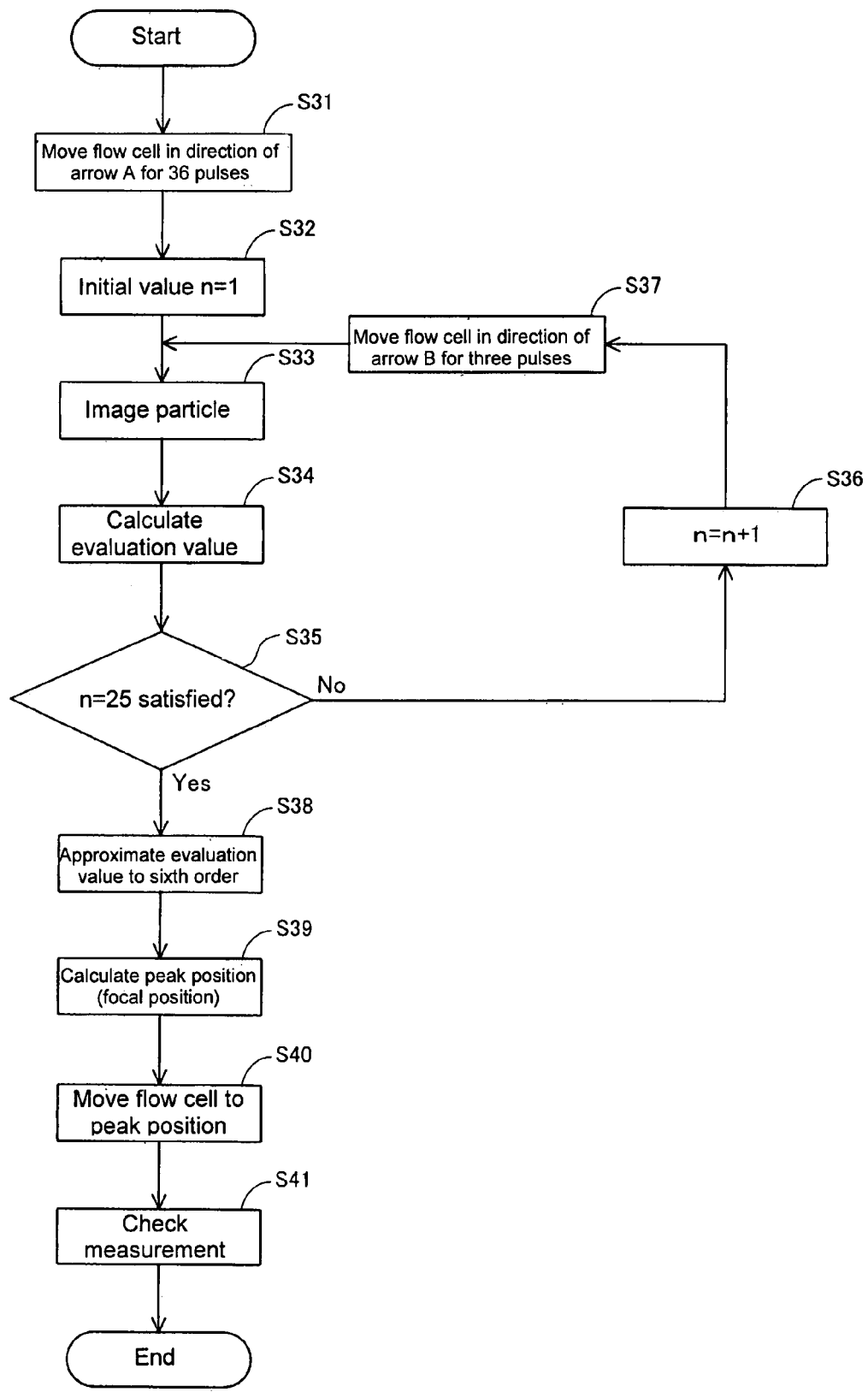

[Fig. 28]
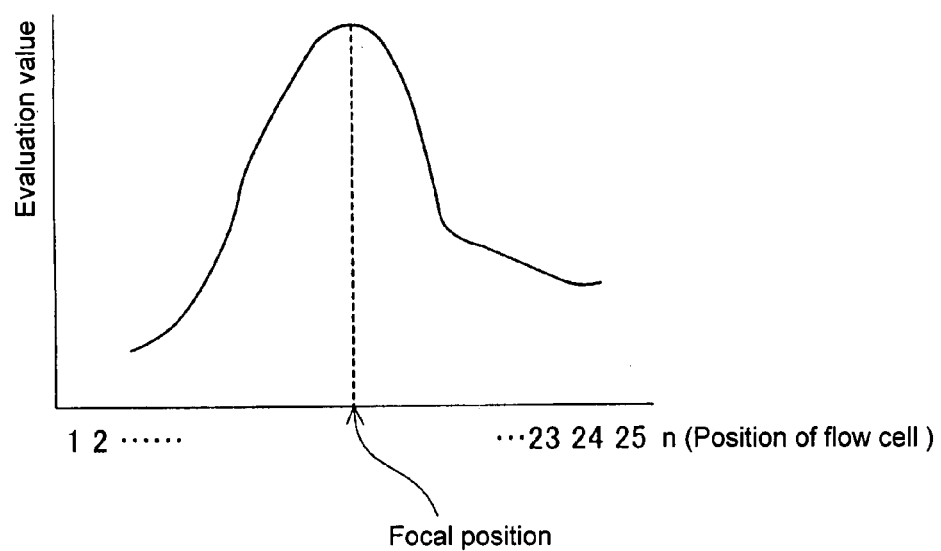

[Fig. 29]
Operation flow of stroboscopic light emitting intensity adjustment
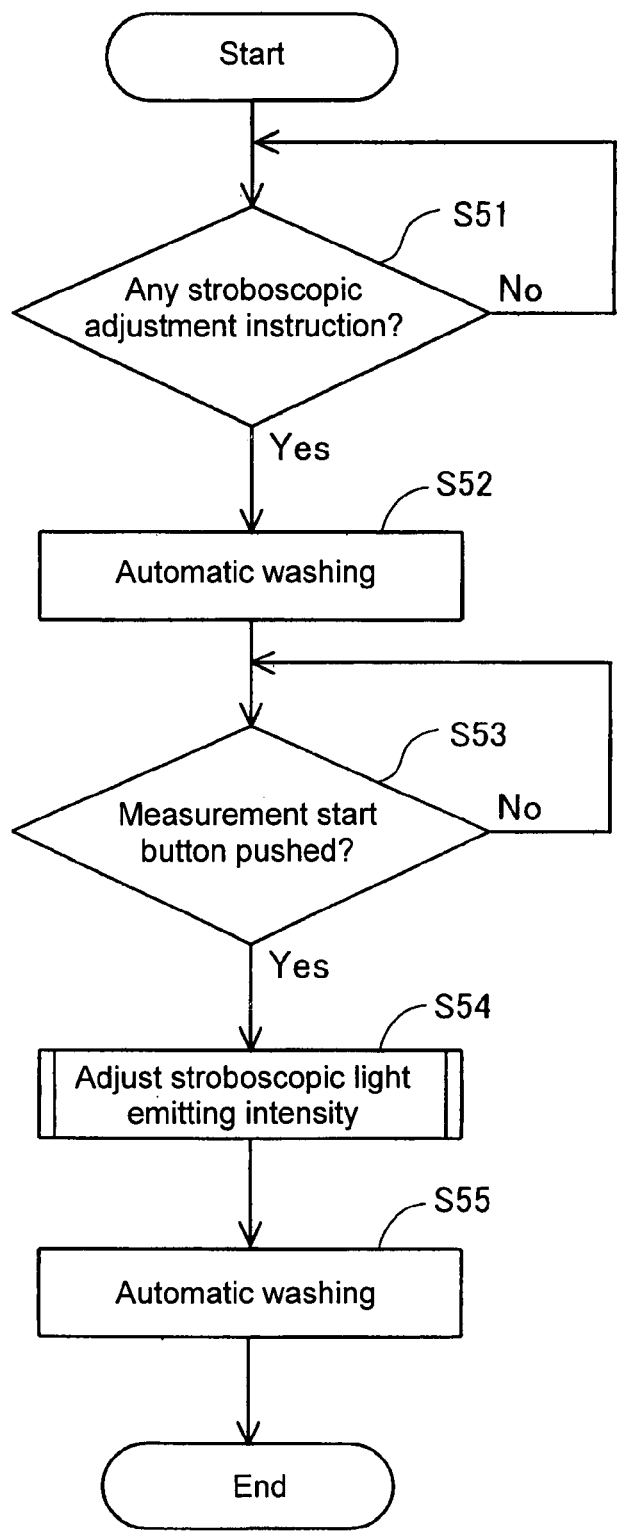

[Fig. 30]
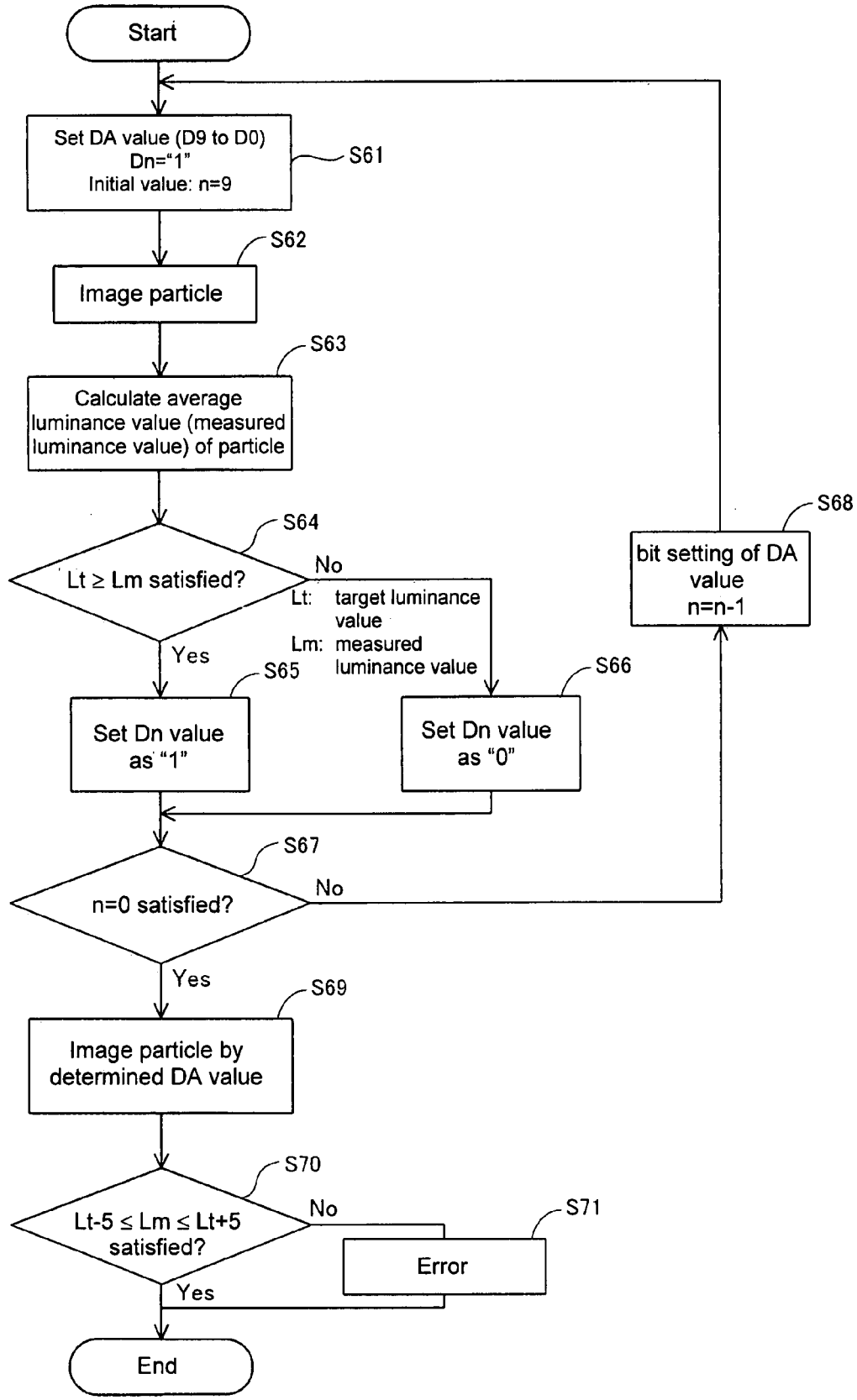

[Fig. 31]

|  | D9 | D8 | D7 | D6 | D5 | D4 | D3 | D2 | D1 | D0 |
|---|---|---|---|---|---|---|---|---|---|---|
| n=9 | 1 | 0 | 0 | 0 | 0 | 0 | 0 | 0 | 0 | 0 |
| n=8 | 1 | 0 | 0 | 0 | 0 | 0 | 0 | 0 | 0 | 0 |
| n=7 | 1 | 0 | 1 | 0 | 0 | 0 | 0 | 0 | 0 | 0 |
| n=0 | 1 | 0 | 1 | 0 | 0 | 0 | 1 | 0 | 1 | 0 |

PARTICLE IMAGE ANALYZING APPARATUS

RELATED APPLICATIONS

This application claims priority under 35 U.S.C. § 119 to Japanese Patent Application No. JP2006-135033 filed May 15, 2006, the entire content of which is hereby incorporated by reference.

FIELD OF THE INVENTION

The present invention relates to particle image analyzing apparatuses, in particular, to a particle image analyzing apparatus for analyzing the image of the particle.

BACKGROUND OF THE INVENTION

A particle image imaging device capable of imaging particles, and a particle image analyzing apparatus for analyzing the image of the particles are conventionally known (see e.g., EP1245945 and Japanese Laid-Open Patent Publication No. 2000-131616).

EP1245945 discloses a particle image analyzing apparatus for mixing a first suspension liquid in which transparent particles are dispersed in water and a second suspension liquid in which non-transparent particles are dispersed in water, thereby electrostatically attaching the non-transparent particles to the transparent particles to make the transparent particles non-transparent, and thereafter, imaging such non-transparent particles, and analyzing the imaged image. In such particle image analyzing apparatus, the degree of circularity of the transparent particle (morphological feature information) is calculated based on the imaged image.

Japanese Laid-Open Patent Publication No. 2000-131616 discloses a particle image imaging device including an zonal light generating unit (dark field illuminating unit) for converting the exit window from the light source to an zonal light, an inner surface reflection mirror for collecting and irradiating the zonal light to the particles dispersed in liquid, an objective lens for receiving the light from the illuminated particles at the inner side of the zonal light, an imaging lens arranged on the optical axis of the objective lens, and an imaging element for imaging the image formed by the imaging lens. The particles in the light scattering medium can be clearly imaged with the particle image imaging device of Japanese Laid-Open Patent Publication No. 2000-131616.

However, the particle image analyzing apparatus of EP1245945 requires for the preparation of the first suspension liquid in which the transparent particles are dispersed in water and the second suspension liquid in which the non-transparent particles are dispersed in water, and furthermore, mixing of the first suspension liquid and the second suspension liquid in order to image the transparent particles, and thus a great number of man hours and trouble are required in the imaging step of the transparent particles. The imaging step thus becomes complicating.

Furthermore, in Japanese Laid-Open Patent Publication No. 2000-131616, the laser light, which coherence is lowered by a coherence lowering element, is converted to the zonal light and then illuminated, and a translucent plate having a roughness of about the laser wavelength and a spatial filter in which the portion distant from the optical axis has higher light transmission than the optical axis are used to enable imaging of fine particles in the light scattering medium, but no description is made on analyzing the imaged particle image, in particular, no description is made on how the transparent particle image is analyzed in order to acquire the morphological feature information of the transparent particle.

SUMMARY OF THE INVENTION

The scope of the present invention is defined solely by the appended claims, and is not affected to any degree by the statements within this summary.

A particle image analyzing apparatus according to a first aspect of the present invention is a particle image analyzing apparatus for analyzing an image of a particle, the particle image analyzing apparatus comprising: an illuminating unit for providing dark field illumination a particle; an imaging unit for capturing an image by imaging the illuminated particle; and an image processing unit for extracting a particle image from the image captured by the imaging unit based on a threshold value larger than a luminance value substantially corresponding to the background of the particle image, and analyzing the extracted particle image to obtain morphological feature information indicating the morphological feature of the particle A particle image analyzing apparatus according to a second aspect of the present invention is a particle image analyzing apparatus for analyzing an image of a particle; the particle image analyzing apparatus comprising: an illuminating unit capable of illuminating the particle by bright field illumination and by dark field illumination; switching means for switching the illuminating unit to either the bright field illumination or the dark field illumination; an imaging unit for capturing an image by imaging the particle illuminated by either the bright field illumination or the dark field illumination switched by the switching means; and an image processing unit for extracting a particle image from the imaged image acquired by the imaging unit and analyzing the extracted particle image to obtain morphological feature information indicating the morphological feature of the particle; wherein when the imaging unit images the particle illuminated by bright field illumination, the particle image is extracted from the imaged image by the bright field illumination based or a threshold value smaller than a luminance value substantially corresponding to the background of the captured image; and when the imaging unit images the particle illuminated by dark field illumination, the particle image is extracted from the captured image by the dark field illumination based on a threshold value greater than the luminance value substantially corresponding to the background of the captured image.

A particle image analyzing apparatus according to a third aspect of the present invention is a particle image analyzing apparatus for analyzing an image of a particle, the particle image analyzing apparatus comprising: an image acquiring unit for acquiring a particle image containing a plurality of pixels, the plurality of pixels including particle pixels indicating the particle and background pixels indicating the background; and an image processing unit for categorizing pixels having a greater luminance than a predetermined threshold value as particle pixels and categorizing pixels having a smaller luminance than the predetermined threshold value as the background pixels.

BRIEF DESCRIPTION OF THE DRAWINGS

The invention, together with objects and advantages thereof, may best be understood by reference to the following description of the presently preferred embodiment together with the accompanying drawings in which:

FIG. 1 is a perspective view showing the entire configuration of a particle image analyzing apparatus according to one embodiment of the present invention;

FIG. 2 is a schematic view showing the entire configuration of the particle image analyzing apparatus according to the embodiment shown in FIG. 1;

FIG. 3 is a cross sectional view describing the flow of the particle suspension liquid and the sheath liquid in the flow cell according to the embodiment shown in FIG. 2;

FIG. 4 is a perspective view showing a flow cell, a supplying mechanism section, and a supporting mechanism section of the particle image analyzing apparatus according to one embodiment;

FIG. 5 is a plan view of FIG. 4;

FIG. 6 is a side view of FIG. 4;

FIG. 7 is a perspective view showing the supporting mechanism section of the particle image analyzing apparatus according to one embodiment;

FIG. 8 is a plan view showing an inner configuration of the particle image processing device according to the embodiment shown in FIG. 1;

FIG. 9 is a plan view partially showing the particle image processing device according to the embodiment shown in FIG. 5;

FIG. 10 is a front view of the particle image processing device according to the embodiment shown in FIG. 5;

FIG. 11 is a plan view showing a ring slit to be attached to an auxiliary lens in the dark field illumination;

FIG. 12 is a perspective view showing the auxiliary lens and the ring slit;

FIG. 13 is a conceptual view describing the principle of the dark field illumination;

FIG. 14 is a block diagram showing a configuration of the particle image processing device of the particle image analyzing apparatus according to the embodiment shown in FIG. 1;

FIG. 15 is a schematic view describing the image processing operation of the particle image analyzing apparatus according to the embodiment shown in FIG. 1;

FIG. 16 is a flow chart showing the processing procedures of an image processing processor of the particle image processing device according to the embodiment shown in FIG. 14;

FIG. 17 is a frame format view describing the set value of coefficients used in Laplacian process by the Laplacian processing circuit of the image processing processor according to the embodiment shown in FIG. 14;

FIG. 18 is a frame format view describing the method of determining a binary threshold value in a binarization process of the image processing processor according to one embodiment;

FIG. 19 is a frame format view describing the method of determining a binary threshold value in the binarization process of the image processing processor according to one embodiment;

FIG. 20 is a frame format view showing the content of a prime code data storage memory used in a prime code/multiple point information acquiring process by the binarization processing circuit of the image processing processor according to the embodiment shown in FIG. 14;

FIG. 21 is a frame format view describing the definition of the prime code used in the prime code/multiple point information acquiring process by the binarization processing circuit of the image processing processor according to the embodiment shown in FIG. 14;

FIG. 22 is a frame format view describing the concept of multiple point used in the prime code/multiple point information acquiring process by the binarization processing circuit of the image processing processor according to the embodiment shown in FIG. 14;

FIG. 23 is a frame format view describing the determination principle of whether or not an inner particle image to be used in overlap checking process by an overlap checking circuit of the image processing processor according to the embodiment shown in FIG. 14 exists;

FIG. 24 is a frame format view showing the configuration of one particle data in one frame data transmitted to the image data processing unit from the image processing substrate according to the embodiment shown in FIG. 15;

FIG. 25 is a view describing the law in cutting out the partial image from the entire image of the particle by the image processing substrate according to the embodiment shown in FIG. 6;

FIG. 26 is a flow chart showing the operation procedures of an image analysis processing module of the image data processing unit according to the embodiment shown in FIG. 15;

FIG. 27 is a flow chart describing the operation of automatic focusing adjustment of the flow cell according to one embodiment;

FIG. 28 is a graph of when the relationship between the position of the flow cell and the average luminance value is approximated to the six order function in automatic focusing adjustment of the flow cell according to one embodiment;

FIG. 29 is a flow chart describing the procedures of automatic adjustment of the stroboscopic light emitting intensity of a lamp according to one embodiment;

FIG. 30 is a flow chart describing the operation of automatic adjustment of the stroboscopic light emitting intensity of the lamp according to one embodiment; and FIG. 31 is a view describing the operation of the automatic adjustment of the stroboscopic light emitting intensity of the lamp according to one embodiment.

DETAILED DESCRIPTION OF THE PREFERRED EMBODIMENTS

The embodiments embodying the present invention will now be described based on the drawings.

FIG. 1 is a perspective view showing the entire configuration of a particle image analyzing apparatus including a particle image processing device according to one embodiment of the present invention, and FIG. 2 is a schematic view showing the entire configuration of the particle image analyzing apparatus shown in FIG. 1. FIGS. 3 to 12 are views describing the configuration of the particle image processing device according to the embodiment shown in FIG. 1, and FIG. 13 is a view describing the measurement principle by the dark field illumination. FIG. 14 is a block diagram showing a configuration of the particle image processing device of the particle image analyzing apparatus according to the embodiment shown in FIG. 1. First, the entire configuration of the particle image analyzing apparatus including the particle image processing apparatus 1 according to one embodiment of the present invention will be described with reference to FIGS. 1 to 14.

The particle image analyzing apparatus is used to manage the quality of fine ceramic particles, and powders such as pigment and cosmetic powder. The particle image analyzing apparatus is configured by the particle image processing apparatus 1, and an image data analyzing device 2 electrically connected to the particle image processing apparatus 1 using an electrical signal line (USB (Universal Serial Bus) 2.0 cable in the present embodiment) 300, as shown in FIGS. 1 and 2.

The particle image processing apparatus 1 is provided to perform the processes of imaging the particles in the liquid, and analyzing the imaged particle image to obtain the morphological feature information (size, shape etc.) of the particle. The particles analyzed by the particle image processing apparatus 1 include fine ceramic particles and powder such as pigment and cosmetic powder. The particle image processing apparatus 1 is entirely covered by a cover 1a, as shown in FIG. 1. The cover 1a has a function of shielding light, and has a heat insulating material (not shown) to retain heat attached to the inner surface.

As shown in FIG. 8, a Peltier element 1b and a fan 1c are attached to the particle image processing apparatus 1 to maintain the inside of the particle image processing apparatus 1 covered by the cover 1a (see FIG. 1) at a predetermined temperature (approx. 25° C.). The shift in focal length in time of imaging caused by change in temperature, and change in properties such as viscosity and specific gravity of the sheath liquid to be hereinafter described are suppressed by maintaining the inside of the particle image processing apparatus 1 at a predetermined temperature (approx. 25° C.) by the cover 1a, the Peltier element 1b and the fan 1c.

Furthermore, a switch can be made to one of either the bright field illumination or the dark field illumination in the particle image processing apparatus 1 according to the present embodiment depending on the measuring object when imaging the particles. For instance, the particle is imaged by the dark field illumination if the measuring object is a transparent particle or a particle close to transparent, and the particle is imaged by the bright field illumination if the measuring object is a non-transparent particle.

The image data analyzing device 2 is provided to store and analyze the particle image processed by the particle image processing apparatus 1, and to automatically calculate and display the size, shape and the like of the particle. The image data analyzing device 2 includes a personal computer (PC) equipped with an image display unit (display) 2a for displaying the particle image and a keyboard 2c, as shown in FIGS. 1 and 2.

As shown in FIG. 2, the particle image processing apparatus 1 includes a fluid mechanism unit 3 for forming the flow of particle suspension liquid, an illumination optical system 4 for irradiating light to the flow of the particle suspension liquid, an imaging optical system 5 for imaging the flow of the particle suspension liquid, an image processing substrate 6 for performing cut-out process and the like of the partial image (particle image) from the imaged image imaged by the imaging optical system 5, and a CPU substrate 7 for controlling the particle image processing apparatus 1. The illumination optical system 4 and the imaging optical system 5 are arranged at positions facing each other with the fluid mechanism unit 3 in between.

The fluid mechanism unit 3 includes a flow cell 8 made of transparent quartz, a supplying mechanism section 9 for supplying the particle suspension liquid and the sheath liquid to the flow cell 8, and a supporting mechanism section 10 for supporting the flow cell 8. The flow cell 8 has a function of converting the flow of the particle suspension liquid to a flat flow by sandwiching the relevant flow with the flow of sheath liquid flowing on both sides of the particle suspension liquid. The flow cell 8 has a concave part 8a of longitudinal shape near the center position on the outer surface of the flow cell 8 on the imaging optical system 5 side, as shown in FIGS. 2 and 3. The particle suspension liquid flowing through the flow cell 8 is formed so as to be imaged through the concave part 8a of the flow cell 8.

As shown in FIG. 2, the supplying mechanism section 9 includes a supply part 9b having a sample nozzle 9a (see FIG. 2) for supplying the particle suspension liquid to the flow cell 8, a supply port 9c for supplying the particle suspension liquid to the supply part 9b, a sheath liquid container 9d for accommodating the sheath liquid, a sheath liquid chamber 9e for temporarily accumulating the sheath liquid, and a waste liquid chamber 9f for accumulating the sheath liquid that has passed through the flow cell 8.

As shown in FIGS. 4 to 7, the supporting mechanism section 10 is configured to support the flow cell 8 so as to be movable in the direction of the arrow A and the direction of the arrow B, so that the distance with respect to the objective lens 61 to be hereinafter described can be changed. The supporting mechanism section 10 includes a flow cell attachment member 11, a linear movement guide 12 made up of a slide rail 12a for supporting the flow cell attachment member 11 so as to be slidable in the direction of the arrow A and the direction of the arrow B and a slider 12b, a driving force relay part 13, a linear movement guide 14 made up of a slide rail 14a for supporting the driving force relay part 13 so as to be slidable in the direction of the arrow A and the direction of the arrow B and a slider 14b, a supporting plate 15 to be attached with the linear movement guide 12 and the linear movement guide 14, and a drive motor 16 for slide moving the driving force relay part 13. Furthermore, the supporting mechanism section 10 includes a light transparent sensor 17 for detecting that the flow cell 8 has reached the end in the direction of the arrow A, a light transparent sensor 18 for detecting that the flow cell 8 has reached the end in the direction of the arrow B, a side plate 19 securely attached on the flow cell attachment member 11 side of the supporting plate 15, side plates 20 and 21 attached so as to face each other on the driving force relay part 13 side of the supporting plate 15, a motor attachment plate 22 attached to the side plate 21, four motor attachment column parts 23 attached to the motor attachment plate 22, a compression coil spring 24 attached between the flow cell attachment member 11 and the side plate 19, and a stopper member 25 attached to the flow cell attachment member 11.

A contacting part 11a having an L-shape in plan view is integrally arranged on the flow cell attachment member 11, as shown in FIGS. 4 to 7.

The driving force relay part 13 includes a plate shaped relay member 13a having a screw hole (not shown) on the inside, a screw shaft 13b (see FIGS. 5 and 7) to be inserted to the screw hole of the relay member 13a, and a coupling 13c for transmitting the driving force of the drive motor 16 from the motor shaft 16a to the screw shaft 13b (see FIGS. 5 and 7). The relay member 13a is configured to slide in the direction of the arrow A and the direction of the arrow B by the linear movement guide 14 when the drive motor 16 rotates the screw shaft 13b through the motor shaft 16a and the coupling 13c. A projection 13d having a screw hole (not shown) is arranged in the relay member 13a at a position corresponding to the L-shaped contacting part 11a. A screw 13e having the distal end projecting towards the L-shaped contacting part 11a side is attached to the screw hole of the projection 13d. Detection strips 13f and 13g to be detected by the light transparent sensors 17 and 18, respectively, are attached to the relay member 13a.

The drive motor 16 is a stepping motor that is controlled by the CPU substrate 7 of the particle image processing apparatus 1. Furthermore, the screw hole (not shown) of the relay member 13a and the screw shaft 13b are configured so that the flow cell 8 moves about 0.37 μm every time one pulse is applied to the drive motor 16. The image data analyzing device 2 of the particle image analyzing apparatus according to the present embodiment controls the drive motor 16 to adjust the distance between the flow cell 8 and the objective lens 61 to be hereinafter described, so that the focus of a CCD camera 82 of an imaging unit 80 to be hereinafter described is automatically focused on the particles in the particle suspension liquid flowing through the flow cell 8. This aspect will be described in detail below.

The sensor 17 has a function of detecting whether the relay member 13a has reached the end in the direction of the arrow A by detecting the detection strip 13f attached to the relay member 13a. The sensor 18 has a function of detecting whether the relay member 13a has reached the end in the direction of the arrow B by detecting the detection strip 13g attached to the relay member 13a. The sensors 17 and 18 are able to detect whether the flow cell 8 has reached the end position in the direction of the arrow A and the direction of the arrow B, since the relay member 13a and the flow cell attachment member 11 to be attached with the flow cell 8 slide integrally, as hereinafter described. The flow cell 8 is thereby suppressed from contacting the objective lens 61 or a condenser lens 53.

The flow cell attachment member 11 is biased in the direction of the arrow A by the compression coil spring 24 attached between the flow cell attachment member 11 and the side plate 19. The L-shaped contacting part 11a of the flow cell attachment member 11 is thereby pressed against the distal end of the screw 13e of the projection 13d of the relay member 13a. Therefore, when the relay member 13a slides, the flow cell attachment member 11 integrally slides with the relay member 13a. The stopper member 25 arranged on the flow cell attachment member 11 is arranged to suppress the flow cell attachment member 11 from moving in the direction B further from the predetermined position.

The illumination optical system 4 includes an irradiation unit 30, a light attenuating unit 40 installed on the flow cell 8 side of the irradiation unit 30, and a light collecting unit 50 installed on the flow cell 8 side of the light attenuating unit 40, as shown in FIGS. 2 and 8. The irradiation unit 30 is arranged to irradiate the light towards the flow cell 8.

As sown in FIGS. 9 and 10, the irradiation unit 30 includes a lamp 31 serving as a light source, a field diaphragm section 32, and a bracket 33 for supporting the lamp 31 and the field diaphragm section 32. The field diaphragm section 32 is arranged to adjust the field range that can be imaged by the imaging unit 80, to be hereinafter described. The lamp 31 has the light emitting voltage controlled by the image data analyzing device 2. The voltage value applied to the lamp 31 is controlled by a DA value represented by ten digit binary numbers in the image data analyzing device 2. The DA value can be varied in 1024 steps from "0000000000" to "1111111111", and corresponds to voltage values of about 400V to 1000V.

The lamp 31 periodically irradiates a pulse light every 1/60 seconds when imaging the particles. The particle images worth of 60 frames are thereby imaged in one second. In normal measurement, the particle images worth of 3600 frames are imaged in one minute in one measurement.

In the present embodiment, the image data analyzing device 2 of the particle image analyzing apparatus is configured to automatically adjust the stroboscopic light emitting intensity of the lamp 31. This aspect will be described later in detail.

The light attenuating unit 40 is arranged to adjust the intensity of the light by attenuating the light from the irradiation unit 30. The light attenuating unit 40 includes a fixed light attenuating section 40a fixedly attached with respect to the irradiation unit 30, a movable light attenuating section 40b attached so as to be movable in the Y direction with respect to the irradiation unit 30, and a bracket 40c for supporting the fixed light attenuating section 40a and the movable light attenuating section 40b, as shown in FIG. 9.

The fixed light attenuating section 40a includes a fixed light attenuating filter 41, two continuous screws 42, a rail member 43, and a positioning pin 44, as shown in FIGS. 9 and 10. The fixed light attenuating filter 41 is configured to be detachably attached to the rail member 43 so as to be interchangeable with another fixed light attenuating filter 41 having a different light attenuating rate. Two continuous screws 42 are arranged to attach the fixed light attenuating filter 41 to the rail member 32. The positioning pin 33 has a function of positioning the fixed light attenuating filter 41 with respect to the rail member 43. In the present embodiment, the fixed light attenuating filter 41 of the fixed light attenuating section 40a is detached when performing imaging by the dark field illumination to sufficiently ensure the amount of light in time of imaging by the dark field illumination.

The movable light attenuating section 40b includes a movable light attenuating filter 45, a drive mechanism part 47 for moving the movable light attenuating filter 45 along a linear movement guide 46 (see FIG. 10), a detection strip 48 attached to the movable light attenuating filter 45 (see FIG. 9), and a light transparent sensor 49, attached to the bracket 40c, for detecting the detection strip 48, as shown in FIGS. 9 and 10. The movable light attenuating filter 45 is installed on the irradiation unit 30 side of the fixed light attenuating section 40a, and is configured to be movable between an operation position of attenuating the light from the irradiation unit 30 and an evacuation position of not influencing the light from the irradiation unit 30. The drive mechanism part 47 includes an air cylinder 47b serving as a drive source with a piston rod 47a, and a drive transmission member 47d connected to the piston rod 47a of the air cylinder 47b by way of a coupling member 47c. The drive transmission member 47d is attached to the movable light attenuating filter 45. The movable light attenuating filter 45 is attached so as not to be readily changed with another movable light attenuating filter having a different light attenuating rate, different from the fixed light attenuating filter 41. The movable light attenuating filter 45 is used to adjust the amount of light when switching the magnification by a relay lens (lens 88 and lens 89) to be hereinafter described.

The light collecting unit 50 is arranged to collect the light dimmed by the light attenuating unit 40 towards the flow cell 8. The light collecting unit 50 includes an auxiliary lens 51, an aperture stop 52 installed on the flow cell 8 (see FIG. 10) side of the auxiliary lens 51, a condenser lens 53 installed on the flow cell 8 side of the aperture stop 52, a diaphragm adjustment section 54 for adjusting the numerical aperture of the aperture stop 52, and a bracket 55, as shown in FIGS. 9 and 10. The aperture stop 52 is arranged to adjust the amount of light from the irradiation unit 30 side.

In the present embodiment, a ring slit 150 having a light shielding part 150a at the center is attached to the auxiliary lens 51 when performing the dark field illumination, as shown in FIGS. 11 and 12. The ring slit 150 includes the light shielding part 150a, a rim part 150b and a coupling part 150c for connecting the light shielding part 150a and the rim part 150b. The ring slit 150 is attached by being fitted into a ring attachment part 51a of the auxiliary lens 51. The light irradiated from the lamp 31, to be hereinafter described, is thus prevented from directly entering the objective lens 61. The light shielding part 150b of the ring slit 150a is set with a minimum size that does not allow the light from directly entering the objective lens 61. The aperture portion thereby enlarges, and the light of an amount necessary for imaging is irradiated onto the particles. The aperture of the aperture stop 52 is set so as to be a maximum by the diaphragm adjustment section 54 when performing the dark field illumination.

The measurement principle in the dark field illumination will now be described. In the dark field illumination, the light collected by the condenser lens 53 is prevented from directly entering the objective lens 61 by attaching the ring slit 150 to the auxiliary lens 51, as shown in FIG. 13. That is, in the dark field illumination, only the light hit and diffracted by the sample (particle) 160 enters the objective lens 61, thereby forming a sample image (particle image). The light that does not hit the sample (particle) 160 does not enter the objective lens 61, and thus the background appears dark (have small luminance value) compared to the sample image (particle image). The dark field illumination is preferably used when imaging transparent particles since the difference in the luminance values of the background and the particle image of the imaged image in the dark field illumination becomes larger than the difference in luminance values of the background and the particle image of the imaged image in the bright field illumination.

In the bright field illumination, the light hit and shielded by the sample (particle) does not enter the objective lens 61, or enters the objective lens with weaker intensity by detaching the ring slit 150. The light that does not hit the sample (particle) directly enters the objective lens 61. Thus, in the bright field illumination, the background of the imaged image appears bright (have large luminance value) compared to the sample image (particle image).

The imaging optical system 5 is configured by the objective lens unit 60, the imaging lens unit 70, and the imaging unit 80, as shown in FIGS. 2 and 8.

The objective lens unit 60 is arranged to enlarge the optical image of the particles in the particle suspension liquid flowing through the flow cell 8 (see FIG. 10) irradiated by the light from the illumination optical system 5. The objective lens unit 60 includes the objective lens 61, an objective lens holder 62 for holding the objective lens 61, a bracket 63 for supporting the objective lens holder 62, a positioning pin 64 (see FIG. 9), and a fixing screw 65, as shown in FIGS. 9 and 10.

The imaging lens unit 70 includes an imaging lens 71 for imaging the optical image of the particle enlarged in the objective lens unit 60, and a bracket 72 for holding the imaging lens 71.

The imaging unit 80 is arranged to image the particle image captured with the imaging lens unit 70. The imaging unit 80 includes a relay lens box 81, a CCD camera 82, a drive mechanism section 84 for sliding the relay lens box 82 along two linear movement guides 83 in the P direction of FIG. 8, a light shielding cover 85 covering the imaging unit 80, a detection strip 86 attached to the relay lens box 81, and a light transparent sensor 87 for detecting the detection strip 86, as shown in FIG. 8. A lens 88 having an enlargement magnification of two times, and a lens 89 having an enlargement magnification of 0.5 times are incorporated in the relay lens box 81. The lens 88 having an enlargement magnification of two times and a lens 89 having an enlargement magnification of 0.5 times are changeable by sliding the relay lens box 18 in the P direction.

The configuration of the image processing substrate 6 will now be described with reference to FIGS. 2 and 14. As shown in FIG. 14, the image processing substrate 6 is configured by a CPU 91, a ROM 92, a main memory 93, an image processing processor 94, a frame buffer 95, a filter test memory 96, a background correction data memory 97, a prime code data storage memory 98, a vertex data storage memory 99, a result data storage memory 100, an image input interface 101, and an USB interface 102. The CPU 91, the ROM 92, the main memory 93 and the image processing processor 94 are connected by a bus (BUS) to exchange data with each other. The image processing processor 94 is connected to the frame buffer 95, the filter test memory 96, the background correction data memory 97, the prime code data storage memory 98, the vertex data storage memory 99, the result data storage memory 100, and the image input interface 101 by an individual bus (BUS). The read and write of data from the image processing processor 94 to the frame buffer 95, the filter test memory 96, the background correction data memory 97, the prime code data storage memory 98, the vertex data storage memory 99, and the result data storage memory 100 are realized, and furthermore, input of data from the image input interface 101 to the image processing processor 94 is realized. The CPU 91 of such image processing substrate 6 is connected to the USB interface 102 by way of a PCI bus. The USB interface 102 is connected to a CPU substrate 7 by way of a USB/RS-232c converter (not shown).

The CPU 91 has a function of executing the computer program stored on the ROM 92 and the computer program loaded in the main memory 93. The ROM 92 is configured by mask ROM, PROM, EPROM, EEPROM and the like. The computer program executed by the CPU 91, data used for the computer program and the like are recorded on the ROM 92. The main memory 93 is configured by SAM, DRAM and the like. The main memory 93 is used in reading the computer program recorded on the ROM 92 and is also used as a work region of the CPU 91 when the CPU 91 executes the computer program.

The image processing processor 94 is configured by FPGA (Field Programmable Gate Array), ASIC (Application Specific Integrated Circuit) and the like. The image processing processor 94 is a processor dedicated for image processing that is equipped with hardware capable of executing image processing such as median filter processing circuit, Laplacian processing circuit, binarization processing circuit, edge trace processing circuit, overlap checking processing circuit, and result data creating circuit. The frame buffer 95, the filter test memory 96, the background correction data memory 97, the prime code data storage memory 98, the vertex data storage memory 99 and the result data storage memory 100 are each configured by SRAM, DRAM etc. The frame buffer 95, the filter test memory 96, the background correction data memory 97, the prime code data storage memory 98, the vertex data storage memory 99 and the result data storage memory 100 are used for storing data when the image processing processor 94 executes the image processing.

The image input interface 101 includes a video digitizing circuit (not shown) with an A/D converter. The image input interface 101 is electrically connected to the CCD camera 82 (imaging unit 80) by a video signal cable 103, as shown in FIGS. 2 and 14. The video signal input from the CCD camera 82 is then A/D converted by the image input interface 101 (see FIG. 14). The digitized image data (particle image) is configured so as to be stored in the frame buffer 95. The USB interface 102 is connected to the CPU substrate 7 by way of the USB/RS-232c (not shown). The USB interface 102 is connected to the image data analyzing device 2 by an electrical signal line (USB 2.0 cable) 300. The CPU substrate 7 is configured by CPU, ROM, RAM and the like, and has a function of controlling the particle image processing apparatus 1.

The image data analyzing device 2 is configured by a personal computer (PC) including the image display unit 2a, the image data processing unit 2b serving as the device main body equipped with the CPU, ROM, RAM, hard disc and the like, and the input device 2c such as keyboard, as shown in FIGS. 1 and 2. An application program for performing analyzing process and statistical process of the image data based on the processing result in the particle image processing apparatus 1 by communicating with the particle image processing apparatus 1 is installed in the hard disc of the image data processing unit 2b. The application program is configured to be executed by the CPU of the image data processing unit 2b. In the present embodiment, automatic adjustment of stroboscopic light emitting intensity of the lamp 31 and automatic focal adjustment of the flow cell 8 to be hereinafter described can be carried out by the control of the image data analyzing device 2.

The operation of the particle image processing apparatus 1 according to one embodiment of the present invention will now be described with reference to FIGS. 2, 3, 8, 14 and 15. First, after the adjustment of the focal of the flow cell 8 is performed, the adjustment of the stroboscopic light emitting intensity of the lamp 31 is performed. This will be hereinafter described in detail. Thereafter, imaging of the background correction image for generating the background correction data is performed. Specifically, the pulse light from the lamp 31 is periodically irradiated at every 1/60 seconds with only the sheath liquid supplied to the flow cell 8, and imaging is performed by the CCD camera 82. A still image (background correction image) for every 1/60 seconds without the particles flowing through the flow cell 8 is imaged by the CCD camera 82 through the objective lens 61. A plurality of background correction images in which the particles are not appeared is retrieved into the image processing substrate 6. One background correction data is thereby generated, as shown in FIG. 15. In the image processing substrate 6, the background correction data is stored in the background correction data memory 97 (see FIG. 14), and also transmitted to the image data processing unit 2b of the image data analyzing device 2 through the electrical signal line (USB 2.0 cable) 300. The received background correction data is saved in a memory in the image data processing unit 2b on the image data analyzing device 2 side. The process of generating the background correction data is executed only once before the start of imaging of the particles.

The particles are then imaged. Specifically, the particle suspension liquid supplied to the supply port 9c shown in FIG. 2 is supplied to the supply part 9b positioned above the flow cell 8. The particle suspension liquid of the supply part 9b is gradually pushed out into the flow cell 8 from the tip of the sample nozzle 9a (see FIG. 2) provided in the supply part 9b. The sheath liquid is also fed from the sheath liquid container 9d to the flow cell 8 through the sheath liquid chamber 9e and the supply part 9b. The particle suspension liquid flows from top to bottom through the flow cell 8 while being narrowed to a hydrodynamic flat shape by being sandwiched by the sheath liquid from both sides, as shown in FIG. 3. The particle suspension liquid is passed through the flow cell 8 and discharged through the waste liquid chamber 9f, as shown in FIG. 2. As described above, the image of the particle is imaged by the imaging section through the objective lens unit 60 in the imaging optical system 5 by irradiating the light from the irradiation unit 30 of the illumination optical system 4 on the flow of the particle suspension liquid narrowed to a flat shape in the flow cell 8 of the fluid mechanism unit 3.

In this case, the pulse light from the lamp 31 (see FIG. 8) is periodically irradiated at every 1/60 seconds on the flow of the particle suspension liquid narrowed to a flat shape in the flow cell 8. The irradiation of the pulse light from the lamp 31 is performed for 60 seconds. A total of 3600 still images of the particle are imaged by the CCD camera 82 through the objective lens 61.

The distance between the center of gravity of the particle to be imaged and the imaging surface of the CCD camera 82 of the imaging unit 80 may be made substantially constant by imaging a flat surface of the flow of the particle suspension liquid with the imaging unit 80. The focused particle image is thereby obtained regardless of the size of the particle.

The imaged image (particle image) imaged by the CCD camera 82 is output to the image processing substrate 6 (see FIG. 14) as a video signal via the video signal cable 103. The image input interface 101 of the image processing substrate 6 A/D converts the video signal from the CCD camera 82 (see FIG. 14) to generate digitized image data. The image data output by the image input interface 101 shown in FIG. 14 is transferred and stored in the frame buffer 95. The cut-out process (extraction) of the partial image (particle image) from the image data by the image processing substrate 6, and transmission of the image processing result data to the image data processing unit 2b are performed with respect to the frame data stored in the frame buffer 95, as shown in FIG. 15. In this case, the following image processes are first executed by the image processing processor 94 (see FIG. 14) of the image processing substrate 6.

FIG. 16 is a flow chart showing the processing procedures of the imaged image of the image processing processor of the particle image processing device according to the embodiment shown in FIG. 14. FIGS. 17 to 24 are views describing the method of processing the imaged image of the image processing processor of the particle image processing device according to the embodiment shown in FIG. 14. The method of processing the imaged image of the image processing processor 94 of the particle image processing apparatus 1 according to one embodiment will now be described with reference to FIGS. 14 to 24.

Regarding the image processing by the image processing processor 94, the image processing processor 94 executes a noise removal process on the particle image (image data) stored in the frame buffer 95 in step S1. That is, a median filter processing circuit is arranged in the image processing processor 94, as described above. The noise such as dust in the particle image is removed by performing the median filter process by the median filter processing circuit. The median filter processing is a process of lining each luminance value of a total of nine pixels including the pixel of interest and the eight pixels in the vicinity thereof in order of large (or small) numerical value, and taking the median (intermediate value) of the pixel values of nine pixels as the luminance value of the pixel of interest.

In step S2, the image processing processor 94 executes the background correction process to correct the intensity unevenness of the light irradiated on the flow of the particle suspension liquid. That is, a Laplacian processing circuit is arranged in the image processing processor 94, as described above. In the background correction process, a comparison computation of the background correction data stored in the background correction data memory 97 acquired in advance and a particle image of after the median filter process is performed by the Laplacian processing circuit, and a correction image in which large portion of the background image is removed from the particle image is generated.

In step S3, the image processing processor 94 executes an edge enhancement process. In the edge enhancement process, the Laplacian process by the Laplacian processing circuit is performed. The Laplacian process is a process of multiplying each luminance value and a corresponding predetermined coefficient for a total of nine pixels including the pixel of interest and the eight pixels in the vicinity thereof, and taking the sum of the multiplication result as the luminance value of the pixel of interest. As shown in FIG. 17, the coefficient corresponding to the pixel of interest (i, j) is assumed as "2", and the coefficient corresponding to four pixels X(i,j−1), X(i,j+1), X(i−1,j), and X(i+1,j) adjacent to the pixel of interest in the up and down direction and in the left and right direction is assumed as "−¼", and the coefficient corresponding to four pixels X(i−1,j−1), X(i+1,j−1), X(i+1,j+1), and X(i−1,j+1) adjacent to the pixel of interest in the diagonal direction is assumed as "0". The luminance value Y (i, j) of the pixel of interest of after the Laplacian process is calculated by the following equation (1). If the result of equation (1) is larger than 255, 255 is output, and if the result of the calculation by equation (1) is a negative number, 0 is output.

$$Y(i,j)=2\times X(i,j)-0.25\times(X(i,j-1)+X(i-1,j)+X(i,j+1)+X(i+1,j))+0.5 \quad (1)$$

In step S4, the image processing processor 94 sets a binary threshold level (binary threshold value) based on the data after the edge enhancement process is performed. That is, a luminance histogram section for executing the binary threshold value setting process is provided in the Laplacian circuit of the image processing processor 94. First, the image processing processor 94 creates a luminance histogram (see FIGS. 18 and 19) from the image data of after the Laplacian process. FIG. 18 shows the luminance histogram of the imaged image by the bright field illumination, and FIG. 19 shows the luminance histogram of the imaged image by the dark field illumination. The image processing processor 94 performs a predetermined smoothing process on the luminance histogram. After obtaining the most frequent luminance value from the luminance histogram of after the smoothing process, the binary threshold value is calculated with the following equation (2) or (3) using the most frequent luminance value.

$$\text{Binary threshold value=most frequent luminance value} \times \alpha(\text{percent})+\beta \quad (2)$$

$$\text{Binary threshold value=most frequent luminance value}+\gamma \quad (3)$$

Equation (2) is applied to the imaged image by the bright field illumination, and equation (3) is applied to the imaged image by the dark field illumination. In equations (2) and (3), α, β and γ are parameters that can be set by the user, and the user is able to change the values of α, β and γ according to the measuring object. The default values (default) of α and β are "90" and "0", respectively. The value of γ is set between 10 and 70.

In step S5, the image processing processor 94 performs a binarization process on the image of after the Laplacian process at the threshold level (binary threshold value) set in the binary threshold value setting process. That is, the collection of pixels having the luminance value smaller than the value calculated in equation (2) is extracted as the particle image for the imaged image by the bright field illumination. The collection of pixels having the luminance value larger than the value calculated in equation (3) is extracted as the particle image for the imaged image by the dark field illumination.

In step S6, the prime code and the multiple point information are acquired with respect to each pixel of the image performed with the binarization process. That is, a binarization processing circuit is arranged in the image processing processor 94. The binarization process and the prime code/multiple point information acquiring process are executed by the binarization processing circuit. The prime code is a binary code obtained for a total of nine pixels including the pixel of interest and the eight pixels in the vicinity thereof, and is defined as below. The prime code data storage memory 98 includes two regions of a prime code storing region 98a and a multiple point number storing region 98b in one word (one bit), as shown in FIG. 20. The prime code storing region 98a is a region consisting of eight bits indicated by bit0 to bit7 in FIG. 20, and the multiple point number storing region 98b is a region consisting of three bits indicated by bit8 to bit10 in FIG. 20. The definition of the prime code will now be explained. The pixel values of P1 to P3 are 0 and the pixel values of P0 and P4 to P8 are 1 for the nine pixels of P0 to P9 of the binarization processed image data, as shown in FIG. 21. If the luminance value corresponding to each of the nine pixels P0 to P8 is greater than or equal to the binary threshold value, the pixel values of P0 to P8 are 1, whereas if the luminance value corresponding to each of the nine pixels P0 to P8 is smaller than the binary threshold value, the pixel values of P0 to P8 are 0. The prime code for this case is as follows. The eight pixels P0 to P7 other than the pixel of interest P8 each corresponds to bit0 to bit7 of the prime code storing region 98a. That is, the prime code storing region 98a is configured so that the pixel values of the eight pixels P0 to P7 are each stored from the low order bit (bit0) to the high order bit (bit7). The prime code thus becomes 11110001 in binary notation, and becomes F1 in hexadecimal notation. The pixel value of the pixel of interest P8 is not included in the prime code.

If the region configured by the pixel of interest and the eight pixels in the vicinity thereof is one part of the boundary of the particle image, that is, if the prime code is 00000000 in binary notation, the multiple point information is obtained. The multiple point is a code indicating the possibility of number of times the relevant pixel is passed in edge trace, to be hereinafter described, where the multiple point information corresponding to all the patterns are stored in the look up table (not shown) in advance. The number of multiple points is obtained by referencing the look up table. With reference to FIG. 22, if the pixel values of P2 and the four pixels of P5 to P8 are 1, and the pixel values of four pixels of P0, P1, P3 and P4 are 0, there is a possibility the pixel of interest P8 is passed twice in edge trace, as shown with arrows C and D in FIG. 22. Therefore, the pixel of interest P8 has two points, and the number of multiple points is 2. The number of multiple points is stored in the multiple point number storing region 98b.

In step S7, the image processing processor 94 creates vertex data. The vertex data creating process is also executed by the binarization processing circuit arranged in the image processing processor 94, similar to the binarization process and the prime code/multiple point information acquiring process. The vertex data is data indicating the coordinate scheduled to start the edge trace, to be hereinafter described. The region of a total of nine pixels including the pixel of interest and the eight pixels in the vicinity thereof is determined as the vertex only when all of the following three conditions (condition (1) to condition (3)) are satisfied.

Condition (1) Pixel value of the pixel of interest P8 is 1.

Condition (2) Pixel values of three pixels (P1 to P3) above the pixel of interest P8 and one pixel (P4) on the left of the pixel of interest P8 are 0.

Condition (3) Pixel values of one pixel (P0) on right of the pixel of interest P8 and at least one pixel of the three pixels (P5 to P7) below the pixel of interest P8 are 1.

The image processing processor 94 searches for the pixel corresponding to the vertex from all the pixels, and stores the created vertex data (coordinate data showing the position of the vertex) in the vertex data storage memory 99.

In step S8, the image processing processor 94 executes the edge trace process. The edge trace processing circuit is arranged in the image processing processor 94, as described above, and the edge trace process is executed by the edge trace processing circuit. In the edge trace process, the coordinate to start the edge trace is first specified from the vertex data, and the edge trace of the particle image is performed from the relevant coordinate based on the prime code and the code for determining the advancing direction stored in advance. The image processing processor 94 calculates the area value of each particle image, number of direct counts, number of diagonal counts, number of corner counts and position in edge trace. The area value of the particle image is the total number of pixels configuring the particle image, that is, the total number of pixels contained on the inner side of the region surrounded by the edges. The number of direct counts is the total number of edge pixels excluding the edge pixels on both ends in a linear interval when the edge pixels of three or more pixels of the particle image are lined in a straight line in the up and down direction or the left and right direction. In other words, the number of direct counts is the total number of edge pixels configuring the linear component extending in the up and down direction or the left and right direction out of the edges of the particle image. The number of diagonal counts is the total number of edge pixels excluding the edge pixels at both ends in the linear interval in the diagonal direction when the edge pixels of three or more pixels of the particle image are lined in a straight line in the diagonal direction. In other words, the number of diagonal counts is the total number of edge pixels configuring the linear component extending in the diagonal direction out of the edges of the particle image. The number of corner counts is the total number of edge pixels in which a plurality of adjacent edge pixels contact each other in different direction (e.g., adjacent to one edge pixel at the upper side, and adjacent to another edge pixel at the left side) out of the edge pixels of the particle image. In other words, the number of corner counts is the total number of edge pixels configuring the corner of the edges of the particle image. The position of the particle image is determined by the coordinates of the right end, left end, upper end and lower end of the particle image. The image processing processor 94 stores the data of the above calculation result in an internal memory (not shown) incorporated in the image processing processor 94.

In step S9, the image processing processor 94 executes an overlap checking process of the particles. The overlap checking circuit is arranged in the image processing processor 94, as described above, and the overlap checking process is executed by the overlap checking circuit. In the overlap checking process of the particles, the image processing processor 94 first determines whether or not another particle image (inner particle image) is included in the one particle image (outer particle image) based on the analysis result of the particle image by the edge trace process described above. If the inner particle image exists in the outer particle image, the inner particle image is excluded from the target of extraction of the partial image in the result data creating process to be hereinafter described. The determination principle on whether or not the inner particle image exists will now be described. First, as shown in FIG. 23, two particle images G1 and G2 are selected, and the maximum value $G1_{XMAX}$ and the minimum value $G1_{XMIN}$ of the X coordinate, and the maximum value $G1_{YMAX}$ and the minimum value $G1_{YMIN}$ of the Y coordinate of one particle image G1 are specified. Thereafter, the maximum value $G2_{XMAX}$ and the minimum value $G2_{XMIN}$ of the X coordinate, and the maximum value $G2_{YMAX}$ and the minimum value $G2_{YMIN}$ of the Y coordinate of the other particle image G2 are specified. The particle image G2 is determined to be included in the particle image G1, and thus the inner particle image is determined to be included if all of the following four conditions (condition (4) to condition (7)) are satisfied.

Condition (4) maximum value $G1_{XMAX}$ of the X coordinate of the particle image G1 is larger than the maximum value $G2_{XMAX}$ of the X coordinate of the particle image G2

Condition (5) minimum value $G1_{XMIN}$ of the X coordinate of the particle image G1 is smaller than the maximum value $G2_{XMIN}$ of the X coordinate of the particle image G2

Condition (6) maximum value $G1_{YMAX}$ of the Y coordinate of the particle image G1 is larger than the maximum value $G2_{YMAX}$ of the Y coordinate of the particle image G2

Condition (7) minimum value $G1_{YMIN}$ of the Y coordinate of the particle image G1 is smaller than the maximum value $G2_{YMIN}$ of the Y coordinate of the particle image G2.

The result data of the overlap checking process described above is stored in the internal memory (not shown) of the image processing processor 94.

In step S10, the image processing processor 94 cuts out (extracts) the partial image that includes each particle image specified by the processes of steps S1 to S9 individually from the particle image, and creates image processing result data. The result data creating circuit is arranged in the image processing processor 94, as described above, and the result data creating process is executed by the result data creating circuit. The partial image created by the result data creating process is an image obtained by cutting out a rectangular region including one particle and the surrounding region of the relevant particle determined by margin values set in advance from the particle image. The rectangular region according to the present embodiment refers to region R2, which is wider by three pixels in the up and down direction and in the left and right direction than region R1 determined by the upper end coordinate (YMIN), the lower end coordinate (YMAX), the left end coordinate (XMIN) and the right end coordinate (XMAX) of the particle image shown in FIG. 24.

The image processing result data includes data (XMIN, XMAX, YMIN and YMAX) of the position of the partial image containing the particle image and data of the stored position of the image data in addition to partial image data for all the particle images recognized by image processing in step S10, data on area value (pixel number) of the particle image, number of direct counts, number of diagonal counts, number of corner counts and the like, as shown in FIG. 25. The image processing result data is generated for every one frame. The size of the image processing result data (one frame data) of one frame is a fixed length of 64 kilobytes. Therefore, the size of one frame data does not changed depending on the size of one particle data. One frame data is generated by being overwritten on the previous frame data. In one frame data shown in FIG. 25, only four particle data are embedded since each one particle data is very large. If one particle data length is small or the number of one particle data is few, the previous frame data sometimes remains at the end of one frame data since the data is embedded starting from the head of the one frame data. However, the previous frame data remaining at the end will not be recognized since the image data processing unit 2b or the transfer destination recognizes one particle data in one frame data with the total number of particles in one frame stored in the one particle data. The image processing processor 94 stores the image processing result data created by the result data creating process in the result data storage memory 100. The image processing (extraction of particle image) by the image processing processor 94 is thereby terminated. The image processing processor 94 repeatedly executes a series of image processing through pipeline process, and generates the partial image for every frame for 3600 frames. If the particle image does not exist in the frame, the head data of one particle data in the frame shown in FIG. 25 is overwritten, and the particle information between the header and the footer is filled with "0".

FIG. 26 is a flow chart showing the operation procedures of an image analysis processing module of the image data processing unit according to the embodiment shown in FIG. 15. The operation of the analyzing process of the partial image by the image data processing unit 2b of the image data analyzing device 2 will now be described with reference to FIG. 26.

As described above, application program (image analysis processing module) for performing analyzing process of the partial image is installed on the hard disc of the image data processing unit 2b. The analyzing process of the partial image is executed by the image analysis processing module. In the analyzing process operation of the partial image, the image data processing unit 2b receives the image processing result data (include partial image) for one frame in step S21 shown in FIG. 26. In step S22, the number of particles in the received image processing result data for one frame is acquired.

In step S23, the image data processing unit 2b extracts the partial image from the image processing result data for one frame based on the image data storing position (see FIG. 14). Each process of noise removal process, background correction process, binary threshold value setting process, binarization process and edge trace process is executed in steps S24, S25, S26, S27 and S28. Each process executed in steps S24 to S28 corresponds to each process in steps S1, S2, S4, S5 and S8 in the processing procedure flow of the image processing processor 94 shown in FIG. 16. That is, each process performed in the image processing processor 94 may be performed in the image data processing unit 2b. Each process thus can be performed in the image data processing unit 2b at a condition different from the condition of each process performed in the image processing processor 94. The processes in the image processing processor 94 are hardware processed, whereas the processes in the image data processing unit 2b are software processed.

In step S29, determination is made on whether or not all the partial images for one frame are performed with analyzing process. If determined that all the partial images for one frame are not performed with the analyzing process in step S29, the process returns to step S23, and other partial images are extracted from the image processing result data for one frame based on the image data storing position (see FIG. 25). If, on the other hand, determination is made that all the partial images for one frame are performed with the analyzing process in step S29, the process proceeds to step S30. In step S30, determination is made on whether or not the image processing result data has been received for all (3600) frames. If determined that the image processing result data has not been received for all the frames in step S30, the process returns to step S21 to receive the image processing result data for another one frame. If, on the other hand, determination is made that the image processing result data has been received for all the frames, the process ends. The image analyzing process of the particle image corresponding to the partial images for 3600 frames obtained by imaging the particles for 60 seconds is thereby terminated.

FIG. 27 is a flow chart describing the operation of automatic focusing adjustment of when using the dark field illumination in the particle image imaging device according to the present embodiment. The operation of automatic focusing adjustment in time of the dark field illumination of the particle image imaging device according to the present embodiment will now be described with reference to FIGS. 7 and 27. The sample to be imaged when automatic focusing adjustment is performed is a particle (latex particle) having a substantially uniform size and shape.

First, in step S31, the drive motor 16 is driven by the control of the CPU substrate 7 of the particle image processing apparatus 1, so that the flow cell 8 moves in the direction of the arrow A (direction away from the objective lens 61) in FIG. 9 over 36 pulses (0.37 μm×36=13.32 μm). After setting n=1 in step S32, the particle is imaged for 60 frames in step S33.

In step S34, the average luminance value is obtained for each one of the plurality of imaged particle images. The average luminance values are further averaged to calculate the evaluation value (average luminance value for 60 frames).

In step S35, determination is made on whether or not n=25 is satisfied. If n=25 is satisfied, the process proceeds to step S38. If n=25 is not satisfied, n=n+1 (n=2 herein) is set in step S36, and the flow cell 8 moves in the direction of the arrow B (direction moving closer to the objective lens 61) in FIG. 9 over 3 pulses (0.37 μm×3=1.11 μm) in step S37. The particle is imaged and the evaluation value (average luminance value for 60 frames) is calculated in step S33 and step S34 in such state. Subsequently, the processes from step S33 to S37 are similarly repeated until n=25 is satisfied (until 25th time). That is, in the present embodiment, the flow cell is moved in the direction of the arrow A (direction of moving away from the objective lens 61) in FIG. 9 over 36 pulses (13.32 μm) and then moved in the direction of the arrow B (direction of moving closer to the objective lens 61) in FIG. 9 over three pulses (1.11 μm) for 25 times, and meanwhile, the evaluation value at each position is calculated. The data showing the relationship between the position of the flow cell 8 (value of n) and the evaluation value (average luminance value for 60 frames) of the particle image is obtained.

If n=25 in step S35, the relationship between the evaluation values (average luminance value for 60 frames) calculated in step S33 to step S37 and the positions (value of n) of the flow cell 8 is approximated to the six order function as shown in FIG. 28 in step S38.

In step S39, the maximum value of the six order function shown in FIG. 28 is reviewed to calculate the position (peak position) of the flow cell 8 at where the evaluation value (average luminance value for 60 frames) becomes the largest as the focal position.

In step S40, the flow cell 8 is moved to the peak position (focal position). Thereafter, a check measurement is performed in step S41. The result of the check measurement is checked by the user, and the automatic focusing adjustment is terminated.

In the case of automatic focusing adjustment in the bright field illumination, the relationship between the average values of the area (number of pixels) of a plurality of imaged particle images and the positions (value of n) of the flow cell 8 is approximated to the six order function. Taking into consideration that the area (number of pixels) becomes smaller the more focused, the position (peak position) of the flow cell 8 at where the average value of the area becomes the smallest is calculated as the focal position. The focus is adjusted by moving the flow cell 8 to the calculated peak position.

FIG. 29 is a flow chart describing the automatic adjustment operation of the stroboscopic light emitting intensity of the lamp 31. The automatic adjustment operation of the stroboscopic light emitting intensity of the particle image analyzing apparatus according to the present embodiment will now be described with reference to FIG. 29.

In step S51, determination is made on whether or not adjustment instruction of the stroboscopic light emitting intensity is made in the image display unit (display) 2a of the image data analyzing device 2. If the adjustment instruction is not made, such determination is repeated. If the adjustment instruction is made, the sheath liquid is flowed to the flow cell 8 and the flow cell 8 is automatically washed in step S52.

Subsequently, the sample is injected by the user. The sample used herein is a particle (latex particle) having a substantially uniform size and shape. In the case of the bright field illumination, the latex particle having a particle diameter of 2 μm is injected. In the case of the dark field illumination, the latex particle having a particle diameter of 7 μm is injected.

In step S53, determination is made on whether or not the measurement start button (not shown) is pushed in the image display unit (display) 2a of the image data analyzing device 2. If the measurement start button (not shown) is not pushed, such determination is repeated. If the measurement start button (not shown) is pushed, the stroboscopic light emitting intensity is automatically adjusted in step S54. This will be hereinafter described in detail.

After the adjustment of the stroboscopic light emitting intensity is terminated, the sheath liquid is flowed to the flow cell 8, and the flow cell 8 is again automatically washed in step S55. The adjustment operation of the stroboscopic light emitting intensity is thereby terminated.

FIG. 30 is a flow chart describing the automatic adjustment operation of the stroboscopic light emitting intensity in the dark field illumination, and FIG. 31 is a view showing a specific example of the DA value. The automatic adjustment operation of the stroboscopic light emitting intensity in the dark field illumination will now be described with reference to FIGS. 30 and 31.

In step S61, n=9 is set, and Dn=1 (D9=1 herein) is set. That is, the DA value is set to "1000000000". The DA value is expressed in ten digit binary numbers, and is varied in 1024 steps from "0000000000" to "1111111111", and corresponds to voltage values of about 400V to 1000V. The DA value "1000000000" corresponds to an intermediate value (about 700V) of about 400V to 1000V.

In step S62, imaging of the particles for 20 frames is performed by applying the stroboscopic voltage (about 700V) corresponding to the DA value "1000000000" to the lamp 31. In step S63, the average luminance value (measured luminance value Lm) of the particle images for 20 frames is calculated.

In step S64, determination is made on whether or not Lt (target luminance value)≧Lm (measured luminance value) is satisfied. If Lt (target luminance value)≧Lm (measured luminance value) is satisfied, the value of the DA value (D9) of when n=9 is determined as 1 in step S65. If Lt (target luminance value)≧Lm (measured luminance value) is not satisfied, the value of the DA value (D9) of when n=9 is determined as 0.

In step S67, determination is made on whether or not n=0 is satisfied (reached n=0 or not). If n=0 is satisfied (reached n=0), the process proceeds to step S68. If n=0 is not satisfied (not reached n=0), n=n−1 (n=8 herein) is set in step S69.

Subsequently, the DA value (D8) of when n=8 is determined as 0 or 1 in steps S61 to S67 (D8=0 in FIG. 31). Similarly, the DA value (D7 to D0) of when n=7 to n=0 is determined as 0 or 1, as shown in FIG. 31. In FIG. 31, the value of D9 to D0 of when n=0 becomes the DA value (DA value=1010001010).

In step S69, imaging is performed by the stroboscopic light emitting voltage corresponding to the determined DA value (DA value=1010001010 in FIG. 31). In step S70, determination is made on whether or not the measured luminance value Lm (average luminance value) of the imaged particle satisfies, $$Lt-5 \leq Lm \leq Lt+5 \qquad \text{Eq. (4)}$$

If the measured luminance value Lm satisfies the relationship of equation (4), the automatic adjustment operation of the stroboscopic light emitting intensity is terminated. If the measured luminance value Lm does not satisfy the relationship of equation (4), the image data analyzing device 2 outputs an error in step S71, and the DA value returns to the value before the automatic adjustment.

In the present embodiment, the DA value is determined by the feedback control in the dark field illumination. The stroboscopic light emitting voltage corresponding to the determined DA value is applied to the lamp 31 when measuring the sample.

In the bright field illumination, the DA value is determined by the feedback control so that the luminance value of the background becomes a predetermined value (target luminance value).

In the present embodiment, the luminance value of the particle image of the imaged image can be made large with respect to the luminance of the background of the imaged image by imaging the bright field illuminated transparent particle, as described above. The transparent particle thus can be imaged without performing operations such as having the transparent particles non-transparent before imaging, and thus the imaging step of the transparent particles is simplified. The image imaged using the dark field illumination can be easily analyzed to rapidly obtain the morphological feature information by the image data processing unit 2b. Since the image processing substrate 6 and the image data processing unit 2b are configured so that the particle image is extracted from the imaged image based on the threshold value larger than the luminance value substantially corresponding to the background of the particle image, the particle image of large luminance can be easily extracted from the background of small luminance of the particle image imaged by the dark field illumination.

In the present embodiment, the particle image is readily extracted from the particle image imaged by the dark field illumination based on the threshold value set by equation (3) which sets the threshold value larger than the most frequent luminance value calculated by the histogram section, as described above.

In the present embodiment, the image processing substrate 6 and the image data processing unit 2b extract an appropriate particle image for every one frame by executing the extraction of the particle image for every one frame with respect to the imaged images for 3600 frames, as described above.

In the present embodiment, the image processing substrate 6 and the image data processing unit 2b compare the luminance value of each pixel of the imaged image with the threshold value to extract the particle image, thereby extracting a collection of pixels having a luminance greater than the threshold value as the particle image, as described above.

In the present embodiment, the luminance value substantially corresponding to the background is readily calculated from the histogram using the most frequent luminance value of the imaged image as the luminance value substantially corresponding to the background of the imaged image, as described above.

In the present embodiment, the size and shape of the particle can be measured by the image data processing unit, as described above.

In the present embodiment, the particle image is extracted based on the threshold value smaller than the most frequent luminance value and the extracted particle image is analyzed to obtain the morphological feature information indicating the morphological feature of the particle when processing the imaged image by the bright field illumination, whereas the particle image is extracted based on the threshold value greater than the most frequent luminance value and the extracted particle image is analyzed to obtain the morphological feature information indicating the morphological feature of the particle when processing the imaged image by the dark field illumination, whereby the particle image can be extracted from the imaged image by either one of the illuminations of the bright field illumination or the dark field illumination, and the morphological feature information of the particle can be obtained using one particle image analyzing apparatus, as described above.

In the present embodiment, the image data analyzing device 2 is configured to adjust the stroboscopic light emitting intensity of the lamp 31 based on the luminance value of the particle image, thereby setting the stroboscopic light emitting intensity of the lamp 31 so as to be the luminance value of the particle image of when the particle image clearly appears, as described above.

Furthermore, in the present embodiment, the image data analyzing device 2 is configured so as to adjust the light emitting intensity based on the average luminance value of the particle image, thereby setting the stroboscopic light emitting intensity of the lamp 31 so that the particle image overall has the appropriate luminance, as described above.

In the present embodiment, the image data analyzing device 2 is configured so as to adjust the light emitting intensity based on the difference between the target luminance value and the average luminance value of the particle image, thereby setting the light emitting intensity of the illuminating unit corresponding to the average luminance value at when the different between the target luminance value and the average luminance value becomes the smallest can be set as the light emitting intensity corresponding to the target luminance value, as described above.

In the present embodiment, the size and shape of the particle used in adjusting the stroboscopic light emitting intensity are made substantially uniform, and thus the variation of the luminance value of the particle image extracted from the imaged image of the particle is suppressed, as described above. Therefore, the adjustment of the stroboscopic light emitting intensity is more accurately performed by adjusting the stroboscopic light emitting intensity based on the average luminance value of the particle images.

The embodiments disclosed herein are merely illustrative and should not be construed as being exclusive. The scope of the present invention is defined by the Claims and not by the description of the embodiments, and all modifications of equivalent to the Claims and within the scope are encompassed herein.

For example, an example of a configuration in which the calculation of the binary threshold value and the extraction of the particle image by the binary threshold value are performed for every imaged image when imaging the particle for 3600 frames has been described in the above embodiment, but the present invention is not limited thereto, and a configuration in which the calculation of the binary threshold value is performed only for one frame out of the 3600 frames, and the extraction of the particle image of the imaged image for all 3600 frames is performed by the relevant binary threshold value may be adopted. According to such configuration, the extraction of the particle images of other frames can be performed by the binary threshold value calculated by one frame, and thus the morphological feature information of the particle can be obtained at a higher speed.

In the present embodiment, an example of performing imaging for 20 frames in automatic adjustment of the stroboscopic light emitting intensity has been described, but the present invention is not limited thereto, and the imaging for frames more than 20 frames may be performed or the imaging for frames less than 20 frames may be performed.

In the above embodiment, an example in which both illumination methods of the dark field illumination and the bright field illumination can be used has been described, but the present invention is not limited thereto, and a configuration in which only the dark field illumination is used may be adopted.

Furthermore, in the above embodiment, an example of using the most frequent luminance value as the luminance value substantially corresponding to the background of the particle image has been described, but the present invention is not limited thereto, and the average luminance value of the imaged image may be used.

Moreover, in the above embodiment, an example of using the most frequent luminance value as the luminance value substantially corresponding to the background of the particle image has been described, but the present invention is not limited thereto, and the average luminance value of the imaged image (background correction image) imaged for background correction may be used.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

What is claimed is:

1. A particle image analyzing apparatus for analyzing an image of a particle, the particle image analyzing apparatus comprising:

an illuminating unit for providing dark field illumination a particle;

an imaging unit for capturing an image by imaging the illuminated particle; and an image processing unit for extracting a particle image from the image captured by the imaging unit based on a threshold value larger than a luminance value substantially corresponding to the background of the particle image, and analyzing the extracted particle image to obtain morphological feature information indicating the morphological feature of the particle.

2. The particle image analyzing apparatus according to claim 1, wherein the image processing unit includes calculating means for calculating a luminance value substantially corresponding to the background of the image captured by the imaging unit, and threshold value setting means for setting a threshold value larger than the luminance value calculated by the calculating means, wherein the image processing unit extracts the particle image from the image captured by the imaging unit based on the threshold value set by the threshold value setting means.

3. The particle image analyzing apparatus according to claim 2, further comprising a flow cell through which a plurality of particles flow; wherein the imaging unit is configured to image the plurality of particles flowing through the flow cell over a plurality of times; and the threshold value setting means sets the threshold values and the image processing unit extracts a plurality of particle images from each of the captured image based on the threshold value.

4. The particle image analyzing apparatus according to claim 2, further comprising a flow cell through which a plurality of particles flow; wherein
the imaging unit is configured to image the plurality of particles flowing through the flow cell over a plurality of times; and
the threshold value setting means sets a threshold value by using the captured image in a predetermined number of times and the image processing unit extracts the plurality of particle images from each captured image based on the set threshold value.

5. The particle image analyzing apparatus according to claim 1, wherein the image processing unit extracts the particle image by comparing a luminance value of each pixel of the captured image and the threshold value.

6. The particle image analyzing apparatus according to claim 1, wherein a most frequent luminance value of the captured image is used as the luminance value substantially corresponding to the background of the captured image.

7. The particle image analyzing apparatus according to claim 1, wherein the morphological feature information of the particle includes at least one of size or shape of the particle.

8. The particle image analyzing apparatus according to claim 1, wherein the particle is transparent particle.

9. The particle image analyzing apparatus according to claim 1, further comprising an adjustment section for adjusting the light emitting intensity of the illuminating unit;
the image processing unit extracts the particle image from the captured image and obtains the luminance value related to the extracted particle image; and
the adjustment section adjusts the light emitting intensity based on the luminance value of the particle image.

10. The particle image analyzing apparatus according to claim 9, wherein the luminance value related to the particle image is an average luminance value of each pixel.

11. The particle image analyzing apparatus according to claim 10, wherein the adjustment section adjusts the light emitting intensity based on the difference between a target luminance value of the particle image and the average luminance value thereof.

12. The particle image analyzing apparatus according to claim 9, wherein the size and shape of the particles are substantially uniform.

13. The particle image analyzing apparatus according to claim 1, further comprising a flow cell through which a plurality of particles flow, and a movement mechanism for horizontally moving the flow cell at a predetermined interval between the illuminating unit and the imaging unit; wherein
the imaging unit is configured to capture the image of particles flowing through the flow cell over a plurality of times at each position of the flow cell moved by the movement mechanism;
the image processing unit extracts a plurality of particle images from a plurality of captured images, and obtains the luminance values of the plurality of the extracted particle images; and
the particle image analyzing apparatus is configured to determine the position of the flow cell focused by the imaging unit based on the position of the flow cell and the luminance values of the plurality of the particle images.

14. The particle image analyzing apparatus according to claim 13, the particle image analyzing apparatus is configured to determine the position of the flow cell focused by the imaging unit based on the position of the flow cell and an average luminance value of the plurality of particle images.

15. The particle image analyzing apparatus according to claim 14, the particle image analyzing apparatus is configured to determine the position of the flow cell at where the average luminance value is the highest as a position focused by the imaging unit in a relation between the position of the flow cell and the average luminance value.

* * * * *